(12) United States Patent
Giovannoni et al.

(10) Patent No.: US 6,762,347 B1
(45) Date of Patent: Jul. 13, 2004

(54) NOR GENE COMPOSITIONS AND METHODS FOR USE THEREOF

(76) Inventors: James Giovannoni, 1001 Giles St., Ithaca, NY (US) 14850; Steven Tanksley, 113 Pineview Ter., Ithaca, NY (US) 14850; Julia Vrebalov, 1001 Giles St., Ithaca, NY (US) 14850; Frederick Noensie, 95 Lexington Ave., Apt 6E, New York, NY (US) 10016

( * ) Notice: Subject to any disclaimer, the term of this patent is extended or adjusted under 35 U.S.C. 154(b) by 0 days.

(21) Appl. No.: 09/614,408

(22) Filed: Jul. 12, 2000

Related U.S. Application Data

(60) Provisional application No. 60/143,357, filed on Jul. 12, 1999.

(51) Int. Cl.$^7$ .......................... C12N 15/82; C12N 15/84

(52) U.S. Cl. ...................... 800/286; 800/292; 800/293; 800/294; 435/320.1

(58) Field of Search .............................. 435/320.1, 419, 435/468; 536/23.6; 800/286, 298, 292, 293, 294

(56) References Cited

PUBLICATIONS

Mizukami, Y. et al. Separation of AG function in floral meristem determinacy fro that in reproductive organ identity by expressing antisense AG RNA. 1995, Plant Molecular Biology, Vol. 28, pp. 767–784.*
Waterhouse, P. et al. Virus resistance and gene silencing: killing the messenger. Nov. 1999, Vol. 4, No. 11, pp. 452–457.*
Sandler et al, "Inhibition of gene expression transformed plants by antisense RNA", 1988, Plant Molecular Biology, pp. 301–310.*
Kinzer et al., "Mapping of ripening–related or –specific cDNA clones of tomato (*Lycopersicon esculentum*),"*Theor. Appl. Genet*, 79:489–496, 1990.
Magossian et al., "Ethylene–regulated expression of a tomato fruit ripening gene encoding a proteinase inhibitor I with a glutamic residue at the reactive site," *Proc. Natl. Acad. Sci. USA*, 85:8012–8016, 1988.
Rhodes, "The maturation and ripening of fruits," in: Thimann (ed.), *Senescence in Plants*, pp. 157–205, CRC Press, Boca Raton, Fl., 1980.
Yang, "Biosynthesis and action of ethylene," *HortScience*, 20(1):41–45, 1985.
Aida et al., "Genes involved in organ–separation in arabidopsis: An analysis of the cup–shaped cotyledon mutant," *Plant Cell*, 9:841–857, 1997.
Biggs and Handa, "Temporal regulation of polygalacturonase gene expression in fruits of normal, mutant, and heterozygous tomato genotypes," *Plant Physiol.*, 89:117–125, 1988.

Cordes et al., "Interaction of a developmentally regulated DNA–binding factor with sites flanking two different fruit–ripening genes from tomato," *Plant Cell*, 1:1025–1034, 1989.
Darby, "Isogenic lines of tomato fruit color mutants," *Hort. Res.*, 18:73–84, 1978.
Deikman and Fischer, "Interaction of a DNA binding factor with the 5'–flanking region of an ethylene–responsive fruit ripening gene from tomato," *EMBO. J.*, 7(11):3315–3320, 1988.
Deikman et al., "Organization of ripening and ethylene regulatory regions in a fruit–specific promoter from tomato (*Lycopersicon esculentum*)," *Plant Physiol.*, 100:2013–2017, 1992.
Ganal et al., "Pulsed field gel electrophoresis and physical mapping of large DNA fragments in the Tm–2a region of chromosome 9 in tomato," *Mol. Gen. Genet.*, 215:395–400, 1989.
Ganal et al., "Application of RFLPs, physical mapping, and large DNA technologies to the cloning of important genes from crop plants," *AgBiotech News and Info*, 2(6):835–840, 1990.
Giovannoni, "Molecular and genetic analysis of tomato fruit development and ripening" In *Methods In Plant Molecular Biology*. (Bryant, J. ed.) Academic Press. Vol. 10:725–749, 1993.
Giovannoni et al., "Expression of a chimeric polygalacturonase gene in transgenic rin (ripening inhibitor) tomato fruit results in polyuronide degradation but not fruit softening," *Plant Cell*. 1:53–63, 1989.
Giovannoni et al., "Isolation of molecular markers from specific chromosomal intervals using DNA pools from existing mapping populations," *Nuc. Acids Res.*, 19(23):6553–6558, 1991.
Giovannoni et al., "Polygalacturonase and tomato fruit ripening," Horticultural Reviews. 13:67–103, 1991.
Giovannoni et al., "Molecular genetic analysis of ripening–inhibitor and non–ripening loci of tomato: a first step in genetic map–based cloning of fruit ripening genes," *Molecular and General Genetics*, 248(2): 195–206, 1995.

(List continued on next page.)

Primary Examiner—Elizabeth F. McElwain
Assistant Examiner—Cynthia Collins
(74) Attorney, Agent, or Firm—Fulbright & Jaworski LLP

(57) ABSTRACT

The current invention provides nucleic acid sequences encoding the NOR gene. Compositions comprising this sequence are described, as are plants transformed with such compositions. Further provided are methods for the expression of the NOR gene. The methods of the invention include the direct creation of transgenic plants with the NOR gene by genetic transformation, as well as by plant breeding methods. The sequences of the invention represent a valuable new tool for the creation of transgenic plants, preferably having one or more added beneficial characteristics.

28 Claims, 6 Drawing Sheets

(1 of 6 Drawing Sheet(s) Filed in Color)

OTHER PUBLICATIONS

Gray et al., "Molecular biology of fruit ripening and its manipulation with antisense genes," 19:69–87, 1992.

Gray et al., "The use of transgenic and naturally occuring mutants to understand and manipulate tomoat fruit ripening," *Plant Cell Environ.*, 17:557–571, 1994.

Grierson "Molecular biology of fruit ripening" in *Oxford Surveys of Plant Molecular and Cell Biology*, vol. 3. Milan, B (ad.), Oxford University Press. pp363–383, 1986.

Grierson et al., "Tomato ripening mutants," 1987.

Hamilton et al., "Antisense gene that inhibits synthesis of the hormone ethylene in transgenic plants," *Nature*, 346:284–287, 1990.

Harriman et al., "Molecular cloning of tomato pectin methylesterase gene and its expression in Rugers, ripening inhibitor, nonripening and never ripe tomato fruits," *Plant Physiol.*, 97:80–87, 1991.

Hobson and Grierson, "Tomato" in *Biochemistry of Fruit Ripening*, eds. Seymour et al., Chapman &Hall, 1993.

John et al., "Cloning and characterization of tomato leaf senescence–related cDNAs," *Plant Mol. Biol.*, 33:641–651, 1997.

Klee et al., "Control of ethylene synthesis by expression of a bacterial enzyme in transgenic tomato plants," *Plant Cell*, 3:1187–1193, 1991.

Kramer et al., "Field evaluation of tomatoes with reduced polygalacturonase by antisense RNA." In *Horticultural Biotechnology*, Bennett, A. and O'Neill, S. (eds.) Alan R. Liss. pp347–355, 1990.

Lanahan et al., "The never ripe mutation blocks ethylene perception in tomato," *Plant Cell*, 6:521–530, 1994.

Lincoln and Fischer, "Regulation of gene expression by ethylene in wild–type and rin tomato (*Lycopersicon esculentum*) fruit," *Plant Physiol.*, 88:370–374, 1988.

Lincoln et al., "Regulation of gene expression by ethylene during *Lycopersicon esculentum* (tomato) fruit development," *PNA USA*, 84:2793–2797, 1987.

Martin et al., "Construction of a yeast artificial chromosome library of tomato and identification of cloned segments linked to two disease resistance loci," *Mol. Gen. Genet.*, 233:25–32, 1992.

Martin et al., "Map–based cloning of a protein kinase gene conferring disease resistance in tomato," 262:1432–1436, 1994.

Messeguer et al., "Characterization of the level, target sites and inheritance of cytosine methylation in tomato nuclear DNA," *Plant Mol. Biol.*, 16:753–770, 1991.

Montgomery, "Identification of an ethylene–responsive region in the promoter of a fruit ripening gene," *Proc. Natl. Acad. Sci. USA*, 90:5939–5943, 1993.

Oeller et al., "Reversible inhibition of tomato fruit senescence by antisense RNA," *Science*, 254:437–439, 1991.

Pear et al., "Isolation and characterization of a fruit–specific cDNA and the corresponding genomic clone from tomato," *Plant Mol. Biol.*, 13:639–651, 1989.

Picton et al., "cDNA cloning and characterisation of novel ripening–related mRNAs with altered patterns of accumulation in the *ripening inhibitor (rin)* tomato ripening mutant," *Plant Mol. Biol*, 23:193–207, 1993.

Ray et al., "Identification and sequence determination of a cDNA clone for tomato pectin esterase," *Eur. J. Biochem.*, 174:119–124, 1988.

Robinson and Tomes, "Ripening inhibitor: A gene with multiple effects on ripening," *Rep. Tomato Genet. Coop.*, 18:36–37, 1968.

Sheehy et al., "Molecular characterization of tomato fruit polygalacturonase," Mol. Gen. Genet. 208:30–36, 1987.

Slater et al., "Isolation and characterization of cDNA clones for tomato polygalacturonase and other ripeningrelated proteins," *Plant Mol. Biol.*, 5:137–147, 1985.

Smith et al., "Antisense RNA inhibition of polygalacturonase gene expressing in transgenic tomatoes," *Nature*, 334:724–726, 1988.

Souer et al., "The no apical meristem gene of petunia is required for pattern formation in embryos and flowers and is expressed at meristem and primordia boundaries," *Cell*, 85:159–170 1996.

Spiers and Brady, "Modification of gene expression in ripening fruit," *Aust. J. Plant Physiol.*, 18:519–532, 1991.

Starrett and Latices, "Ethylene and wound–induced gene expression in the preclimacteric phase of ripening avocado fruit and mesocarp discs," *Plant Physiol.*, 103:227–234, 1993.

Tanksley et al., "RFLP Mapping in plant breeding: new tools for an old science," *Bio/Technology*, 7:257–264, 1989.

Tanksley et al., High density molecular linkage maps of the tomato and potato genomes, *Genetics*, 132:1141–1160, 1992.

Theologis, "One rotten apple spoils the whole bushel: the role of ethylene in fruit ripening," *Cell*, 70:181–184, 1992.

Tigchelaar et al., "A new fruit ripening mutant, non–ripening (nor)," *Rep. Tomato Genet. Coop.*, 23:33–34, 1973.

Tigchelaar et al., "Genetic regulation of tomato fruit ripening," *HortSci.*, 13(5):508–513, 1978.

Wilkinson et al., "An ethylene–inducible component of signal transduction encoded by *never–ripe,*" *Science*, 270:1807–1809, 1995.

Yelle et al., "Sink metabolism in tomato fruit: IV. Genetic and biochemical analysis of sucrose accumulation," *Plant Physiol.*, 95:1026–1035, 1991.

Yen et al., "The tomato *high pigment (hp)* locus maps to chromosome 2 and influences plastome copy number and fruit quality," *Theor. Appl. Genet.*, 95:1069–1079, 1997.

Yen et al., "The tomato *never–ripe* locus regulates ethylene–inducible gene expression and is linked to a homolog of the *arabidopsis ETR1* gene," *Plant Physiol.*, 107:1343–1353, 1995.

* cited by examiner

NOR genomic DNA sequence

```
5'-
aggtcaactcaaacatcgtaaattgtgatttctttATGGAAAGTACGG
ATTCATCAACCAGGACACGTCATCAGCCTCAACTCCCACCGGGGTTTC
GATTCCACCCGACGGACGAAGAACTCATCGTCCACTACCTCAAAAAAC
GAGTCGCCGGCGCTCCGATTCCGGTGGATATTATTGGTGAAATTGATC
TTTATAAGTTTGATCCTGGGAACTCCCTGGTActattttcaccactat
atttcttgccctaacttatatagggaaaaagatcggagtcag
cgatgaacaattattgtgtctaattaaatttaaatatgcaatagat
tggtgacgaatttcgttgctaattaattttttagtgataaattaatat
ttttccccttttaatcttcatgtttttatcacaaagttttctatga
ccaacttataaagatttgaactcgatcaatttttttttagaatgaat
gaacttatgttatatagtgatatttaaatgcttttttatatttc
aaaagatatccacgataacgtgtaaaagtgaatttgcaaaaaaaaa
tgtagtaccttttatttaatttattgtagataatttagatttaatt
ttgaatttgtttaatttaaattctgaatcgtataatatttatttaatt
tctatttttgagttttttttggagggtgcttaaaaagtagtattca
caaatataaagtagtggacaaacataaagtagtggacccataatttat
tttttaaaattatattaaaactatttgttaagtttaaattctgaat
tatcttcttatcatgtgtttaacgcagctaAGGCAATATTCGGAGAGC
AAGAATGGTTCTTTTTTAGTCCAAGAGATAGAAAATATCCTAACGGGG
CGAGGCCAAATCGGGCTGCAACATCGGGTTATTGGAAGGCTACCGGAA
CCGACAAGCCGGTTTTTACTTCCGGTGGAACACAAAAGGTTGGGGTAA
AAAAGGCGCTCGTTTTTTACGGCGGTAAACCACCAAAAGGGGTAAAAA
CTAATTGGATCGTGCATGAATACAGAGTTGTAGAAAATAAAACAAATA
ACAAGCCACTTGGTTGTGATAATATTGTTGCCAACAAAAAAGGATCTT
TGAGGgtaagtcctaaattttgcatcgaaactaatttctctatcgtat
cagatagggataagatatacgtatactctaatctccttgaaccacaca
agtactatactagatatgttgttgtagatgacttgattcaactttcaa
attttgatgaaaatgtttaagttatataccatatatatataggcg
tagataaaatttcgataaggggggtttaaatctgaaaaaatggatata
cgaaatagccgaaagaggttcgacatagattattttaaccatataaaa
ataatacaattttcatatatatacgccgtggttaatatgaggaata
ttttatactattaatgtacttaaccaggggcggctctagagttgatg
aaccctctcagcgaaaatttacgttgtatatttaaggtaccttttaat
aattttgtatttatatattaattttgaacctcttgaatataagatta
gacgttgacttagtggtttcaggggttcaaatcactattctttttttc
ctaaccccttaatgaaaatcctgaatcggccactaactttaactggt
tatagaaggttaatcttactagaaaaagcatgaaattctaaccgaca
aagatgtagtcgcccagttagataagacgtttaaattgggcggataga
gttactttatttttcactgtcatatgttactatatattgacacttcac
ttaaagagttatcatatcgatattttactattagtgtacataacaca
aactcgaataaattcaatgtttcattagctagttaattagtctaactt
ttttaaaaaaaaatatttttcttactccacactattttattttatttt
tttgcagCTAGATGATTGGGTTTTATGTCGAATTTACAAGAAGAATAA
CACACAAAGGTCCATAGATGATTTGCATGATATGTTGGGATCGATACC
```

FIG. 5

```
ACAAAATGTACCAAATTCAATATTACAAGGAATAAAGCCTTCAAACTA
TGGTACAATATTGCTCGAAAATGAATCGAATATGTACGATGGAATTAT
GAATAACACGAACGATATTATCAACAATAATAATAGATCCATTCCACA
AATATCGTCAAAGAGAACGATGCATGGAGGTTTGTATTGGAATAACGA
CGAAGCAACAACAACAACAACAACTATTGATAGGAACCATTCTCCAAA
TACAAAAGGTTCCTTGTTGAGAACAACGAGGACGATGGACTTAACAT
GAATAATATTTCGCGAATTACAAATCATGAACAAAGTAGCTCCATTGC
CAATTTCCTGAGCCAGTTTCCTCAAAATCCTTCGATTCAACAACAACA
ACAACAACAAGAAGAAGTATTGGGATCTCTTAATGATGGGGTCGTCTT
TCGACAACCTTATAATCAAGTTACTGGCATGAATTGGAATCACTAAag
atataaaaggcaaaaatagttagccctgtaaaatcaatcgatcaat
caatcatagatatattatatggatttcgtt
-3'
```

FIG. 5
*(Cont'd)*

NOR (CD-11) full length cDNA sequence

5´-
aggtcaactcaaacatcgtaaattgtgatttctttATGGAAAGTACGG
ATTCATCAACCAGGACACGTCATCAGCCTCAACTCCCACCGGGGTTTC
GATTCCACCCGACGGACGAAGAACTCATCGTCCACTACCTCAAAAAAC
GAGTCGCCGGCGCTCCGATTCCGGTGGATATTATTGGTGAAATTGATC
TTTATAAGTTTGATCCATGGGAACTCCCTGGTAAGGCAATATTCGGAG
AGCAAGAATGGTTCTTTTTTAGTCCAAGAGATAGAAAATATCCTAACG
GGGCGAGGCCAAATCGGGCTGCAACATCGGGTTATTGGAAGGCTACCG
GAACCGACAAGCCGGTTTTTACTTCCGGTGGAACACAAAAGGTTGGGG
TAAAAAAGGCGCTCGTTTTTACGGCGGTAAACCACCAAAAGGGGTAA
AAACTAATTGGATCATGCATGAATACAGAGTTGTAGAAAATAAAACAA
ATAACAAGCCACTTGGTTGTGATAATATTGTTGCCAACAAAAAAGGAT
CTTTGAGGCTAGATGATTGGGTTTTATGTCGAATTTACAAGAAGAATA
ACACACAAAGGTCCATAGATGATTTGCATGATATGTTGGGATCGATAC
CACAAAATGTACCAAATTCAATATTACAAGGAATAAAGCCTTCAAACT
ATGGTACAATATTGCTCGAAATGAATCGAATATGTACGATGGAATTA
TGAATAACACGAACGATATTATCAACAATAATAATAGATCCATTCCAC
AAATATCGTCAAGAGAACGATGCATGGAGGTTTGTATTGGAATAACG
ACGAAGCAACAACAACAACAACAACTATTGATAGGAACCATTCTCCAA
ATACAAAAAGGTTCCTTGTTGAGAACAACGAGGACGATGGACTTAACA
TGAATAATATTTCGCGAATTACAAATCATGAACAAAGTAGCTCCATTG
CCAATTTCCTGAGCCAGTTTCCTCAAAATCCTTCGATTCAACAACAAC
AACAACAACAAGAAGAAGTATTGGGATCTCTTAATGATGGGGTCGTCT
TTCGACAACCTTATAATCAAGTTACTGGCATGAATTGGAATCACAAag
atataaaaggcaaaaatagttagccctgtaaaatcaatcgatcaat
caatcatagatatattatatatggatttcgttaaaaaaaaaaaaaaaa
aaaaaaaa
-3´

*FIG. 6*

NOR GENE COMPOSITIONS AND METHODS FOR USE THEREOF

This application claims the priority of U.S. Provisional Application Ser. No. 60/143,357, filed Jul. 12, 1999, the disclosure of which is specifically incorporated herein by reference in its entirety.

The government may own rights in this invention subject to grant numbers USDA-NRICGP 92-373000-7653, USDA-NRICGP 92-373000-1575, Texas Advanced Technology Program 999902037, and USDA-NRICGP 91-373000-6418.

BACKGROUND OF THE INVENTION

1. Field of the Invention

The present invention relates generally to the NOR gene. More specifically, it relates to methods and compositions for the modification of plant phenotypes with the NOR gene.

2. Description of the Related Art

The ripe phenotype is the summation of biochemical and physiological changes occurring at the terminal stage of fruit development rendering the organ edible and desirable to seed dispersing animals and valuable as an agricultural commodity. These changes, although variable among species, generally include modification of cell wall ultrastructure and texture, conversion of starch to sugars, increased susceptibility to post-harvest pathogens, alterations in pigment biosynthesis/accumulation, and heightened levels of flavor and aromatic volatiles (Rhodes, 1980; Hobson and Grierson, 1993). Several of theses ripening attributes translate to decreased shelf-life and high input harvest, shipping and storage practices, particularly via changes in firmness and the overall decrease in resistance to microbial infection of ripe fruit. Currently acceptable techniques for minimizing the consequences of undesirable ripening characteristics include premature harvest, controlled atmosphere storage, pesticide application, and chemically induced ripening to synchronize the timing of maturation. Unfortunately, added production, shipping and processing expenses, in addition to reduced fruit quality, are often the consequence of these practices, challenging both the competitiveness and long term sustainability of current levels of crop production.

Although most fruit display modifications in color, texture, flavor, and pathogen susceptibility during maturation, two major classifications of ripening fruit, climacteric and non-climacteric, have been utilized to distinguish fruit on the basis of respiration and ethylene biosynthesis rates. Climacteric fruit such as tomato, cucurbits, avocado, banana, peaches, plums, and apples, are distinguished from non-climacteric fruits such as strawberry, grape and citrus, by their increased respiration and ethylene biosynthesis rates during ripening (Grierson, 1986). Ethylene has been shown to be necessary for the coordination and completion of ripening in climacteric fruit via analysis of inhibitors of ethylene biosynthesis and perception (Yang, 1985; Tucker and Brady, 1987), in transgenic plants blocked in ethylene biosynthesis (Klee et al., 1991; Oeller et al., 1991; Picton et al., 1993 a), and through examination of the Never-ripe (Nr) ethylene perception mutant of tomato (Lanahan et al., 1994).

Considerable attention has been directed toward elucidating the molecular basis of ripening in the model system of tomato during recent years (reviewed in Spiers and Brady, 1991; Gray et al, 1992 and 1994; Giovannoni, 1993; Theologis 1992 and Theologis et al., 1993). The critical role of ethylene in coordinating cliimactic ripening at the molecular level was first observed via analysis of ethylene inducible ripening-related gene expression (Tucker and Laties, 1984; Lincoln et al., 1987; Maunders et al., 1987; DellaPenna et al., 1989; Starrett and Laties; 1993). Several ripening genes, including ACC synthase and ACC oxidase, have been shown via antisense gene repression to have profound influences on the onset and degree of ripening (Hamilton et al., 1990; Oeller et al., 1991). Although the sum effect of this research has been a wealth of information pertaining to the regulation of ethylene biosynthesis and its role in ripening, the molecular basis of developmental cues which initiate ripening-related ethylene biosynthesis, and additional aspects of ripening not directly influenced by ethylene, remain largely unknown (Theologis et al., 1993).

Single locus mutations which attenuate or arrest the nornal ripening process, and do not ripen in response to exogenous ethylene, have been identified in tomato and are likely to represent lesions in regulatory components necessary for initiation of the ripening cascade, including ethylene biosynthesis (Tigchelaar et al., 1978; Grierson, 1987; Giovannoni, 1993; Hobson and Grierson, 1993; Gray et al., 1994). One such mutation, Nr mutation, has been identified and represents a gene responsible for ethylene perception and/or signal trnasduction and is a tomato homologue of the *Arabidosis Ethylene response* 1 (Etr1) gene (Yen et al., 1995; Wilkinson et al., 1995).

Tomato has served as a model for ripening of climacteric fruit. Ripening-related genes have been isolated via differential gene expression patterns (Slater et al., 1985, Lincoln et al., 1987, Pear et al., 1989, Picton et al., 1993b) and biochemical function (DellaPenna et al., 1986; Sheehy et al., 1987; ray et al., 1988; Biggs and Handa, 1989; Harriman and Handa, 1991; Oeller et al., 1991; Yelle et al., 1991). Promoter analysis of ripening genes has been performed via examination of promoter/reporter construct activities in transient assay systems and transgenic plants. The result has been the identification of cis-acting promoter elements which are responsible for both ethylene and non-ethylene regulated aspects of ripening (Deikman et al., 1992; Montgomery et al., 1993). Trans-acting factors which interact with these promoters also have been identified via gel-shift and footprint experiments, although none have been isolated or cloned (Deikman and Fischer, 1988; Cordes et al., 1989; Montgomery et al., 1993).

The in vivo functions of several ripening-related genes including polygalacturonase, pectinmethylesterase, ACC synthase, ACC oxidase, and phytoene synthase have been tested via antisense gene repression and/or mutant complementation in transgenic tomatoes. For example, the cell wall pectinase, polygalacturonase, was shown to be necessary for ripening-related pectin depolymerization and pathogen susceptibility, however, the inhibition of PG expression had minimal effects on fruit softening (Smith et al., 1988, Giovannoni et al., 1989, Kramer et al., 990). Significant reduction in rates of ethylene evolution resulting in inhibition of most ripening characteristics was observed in both ACC synthase and ACC oxidase antisense mutants (Oeller et al., 1991; Hamilton et al., 1990). Non-ripening antisense fruit were subsequently restored to normal ripening phenotype with the application of exogenous ethylene.

Further analysis of transgenic tomatoes inhibited in ethylene biosynthesis demonstrates that climacteric ripening represents a combination of both ethylene mediated and developmental control (Theologis et al., 1993). Although antisense ACC synthase tomatoes which failed to produce ethylene did not ripen, gene expression analysis demonstrated that several ripening-related genes, including polygalacturonase and E8 are expressed in the absence of ethylene. This observation confirms the presence of a developmental (or non-ethylene regulated) component of ripening. In fact, an ethylene requirement was observed for translation but not transcription of polygalacturonase mRNA, suggesting interaction between ethylene and non-ethylene components of ripening for expression of at least a subset of ripening genes (Theologis et al., 1993).

While the above studies have provided some insight into the ripening process in plants, there is still a great need in the art for novel methods and compositions for the creation of plants having enhanced phenotypes. In particular, there is a need in the art for the isolation the RIN and NOR genes. The isolation of these genes would allow the creation of novel transgenic plants altered in their fruit characteristics and/or ethylene responsiveness, and having one or more added beneficial properties.

SUMMARY OF THE INVENTION

In one aspect, the current invention provides an isolated nucleic acid sequence comprising the NOR gene. In one embodiment of the invention, the NOR gene may be further defined as isolatable from the nucleic acid sequence of SEQ ID NO: 1, SEQ ID NO:6 or SEQ ID NO:7. In particular embodiments of the invention, the invention provides an isolated nucleic acid corresponding to an open reading frame of the NOR cDNA, for example, which may be denoted by the nucleotides as indicated by bold letters in FIG. 6.

In another aspect, the invention provides an isolated nucleic acid sequence having from about 17 to about 1209, about 25 to about 1209, about 30 to about 1209, about 40 to about 1209, about 60 to about 1209, about 100 to about 1209, about 200 to about 1209, about 400 to about 1209, about 600 to about 1209, about 800 to about 1209, or about 1000 to about 1209 contiguous nucleotides of the nucleic acid sequence of SEQ ID NO:6 or SEQ ID NO:7. Similarly, the invention provides such nucleic acid segments from SEQ ED NO:1. In particular embodiments of the invention, the nucleic acid sequences of SEQ ID NO:6 and SEQ ID NO:7 are provided. In particular embodiments of the invention, a nucleic acid sequence of the invention may further comprising an enhancer, such as an intron. A nucleic acid sequence of the invention may also include a transcriptional terminator. Such sequences may be native to the NOR gene or heterologous from potentially any species.

In yet another aspect, the invention provides an expression vector comprising a NOR gene. Such a NOR gene may be in accordance with any of the NOR-containing sequences described herein. The expression vector may comprise the NOR gene operably linked to a native or heterologous promoter, either in sense or antisense orientation relative to the promoter. Potentially any heterologous promoter may be used, for example, a promoter is selected from the group consisting of CaMV 35S, CaMV 19S, nos, Adh, actin, histone, ribulose bisphosphate carboxylase, R-allele, root cell promoter, α-tubulin, ABA-inducible promoter, turgor-inducible promoter, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase and S-E9 small subunit RuBP carboxylase promoter. In still further embodiments of the invention, the expression vector may comprise any selectable marker, for example, a selectable marker selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase.

The expression vector may be either circular, for example, as in the case of a plasmid vector, or could be a linear nucleic acid segment, such as an expression cassette isolated from a plasmid. In particular embodiments of the invention, the vector is a plasmid vector. The expression vector may further comprise other elements, such as a nucleic acid sequence encoding a transit peptide, or potentially any terminator, for example, a heterologous terminator such as the nos terminator.

In still yet another aspect, the invention provides a transgenic plant comprising a stably transformed expression vector, such as those described above. The transgenic plant may be any type of plant, and in particular embodiments of the invention is a tomato plant. In further embodiments of the invention, the transgenic plant may be a fertile $R_0$ transgenic plant. Also included in the invention is a seed of such a fertile $R_0$ transgenic plant, wherein said seed comprises said expression vector. The transgenic plant may be a progeny plant of any generation of a fertile $R_0$ transgenic plant, wherein said $R_0$ transgenic plant comprises said expression vector. The invention also includes a seed of such a progeny plant, wherein said seed comprises said expression vector.

In still yet another aspect, the invention provides a crossed fertile transgenic plant prepared according to the method comprising the steps of: (i) obtaining a fertile transgenic plant comprising a selected DNA comprising a NOR gene; (ii) crossing said fertile transgenic plant with itself or with a second plant lacking said selected DNA to prepare the seed of a crossed fertile transgenic plant, wherein said seed comprises said selected DNA; and (iii) planting said seed to obtain a crossed fertile transgenic plant. In one embodiment of the invention, a seed is provided of such a crossed fertile transgenic plant, wherein said seed comprises said selected DNA. The crossed fertile transgenic plant may be of any species, for example, a tomato plant. The plant may also be inbred or hybrid.

In still yet another aspect, the invention provides a method of manipulating the phenotype of a plant comprising the steps of: (i) obtaining an expression vector comprising a NOR gene in sense or antisense orientation; (ii) transforming a recipient plant cell with said expression vector-and (iii) regenerating a transgenic plant from said recipient plant cell, wherein the phenotype of said plant is altered based on the expression of said NOR gene in sense or antisense orientation. Any method of transforming a plant may be used in accordance with the invention, including, microprojectile bombardment, PEG mediated transformation of protoplasts, electroporation, silicon carbide fiber mediated transformation, or Agrobacterium-mediated transformation. In particular embodiments of the invention, Agrobacterium-mediated transformation is used and the plant is a tomato plant.

In still yet another aspect, the invention provides a method of plant breeding comprising the steps of: (i) obtaining a transgenic plant comprising a selected DNA comprising a NOR gene, and (ii) crossing said transgenic plant with itself or a second plant. The plant may be of any species and may be inbred or hybrid. In particular embodiments of the invention, this method further comprises the steps of: (iii) collecting seeds resulting from said crossing; (iv) growing said seeds to produce progeny plants; (v) identifying a progeny plant comprising said selected DNA; and (vi) crossing said progeny plant with itself or a third plant. In one embodiment of the invention, the second plant and third plant are of the same genotype. The second and third plants may also be inbred plants.

In still yet another aspect, the invention provides a transgenic plant cell stably transformed with a selected DNA comprising a NOR gene. The cell may be from any plant species, for example, a cell from a tomato plant. The selected may comprise any of the NOR gene comprising nucleic acid compositions disclosed herein, for example, the expression vector compositions described herein above. Such compositions include the open reading frame of the NOR gene, as provided in SEQ ID NO:6 or SEQ ID NO:7 and demarcated in FIG. 6.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The file of this patent contains at least one drawing executed in color. Copies of this patent with color drawing(s) will be provided by the Patent and Trademark Office upon request and payment of the necessary fee.

FIG. 5. DNA sequence of the region of tomato chromosome 10 harboring the NOR gene (SEQ ID NO:7). The sense genomic DNA sequence of the complete transcribed region is shown in the 5'–3' orientation. The coding sequence is in upper case while non-translated sequences including the two NOR gene introns are in lower case.

FIG. 6. Corrected DNA sequence of the NOR full-length cDNA (CD-11) (SEQ ID NO:6). The full cDNA sequence is shown in 5'–3' orientation. Lower case letters refer to non-translated portions of the transcript while the upper case letters refer to the translated (coding) sequence.

DETAILED DESCRIPTION OF THE INVENTION

Figure 1:
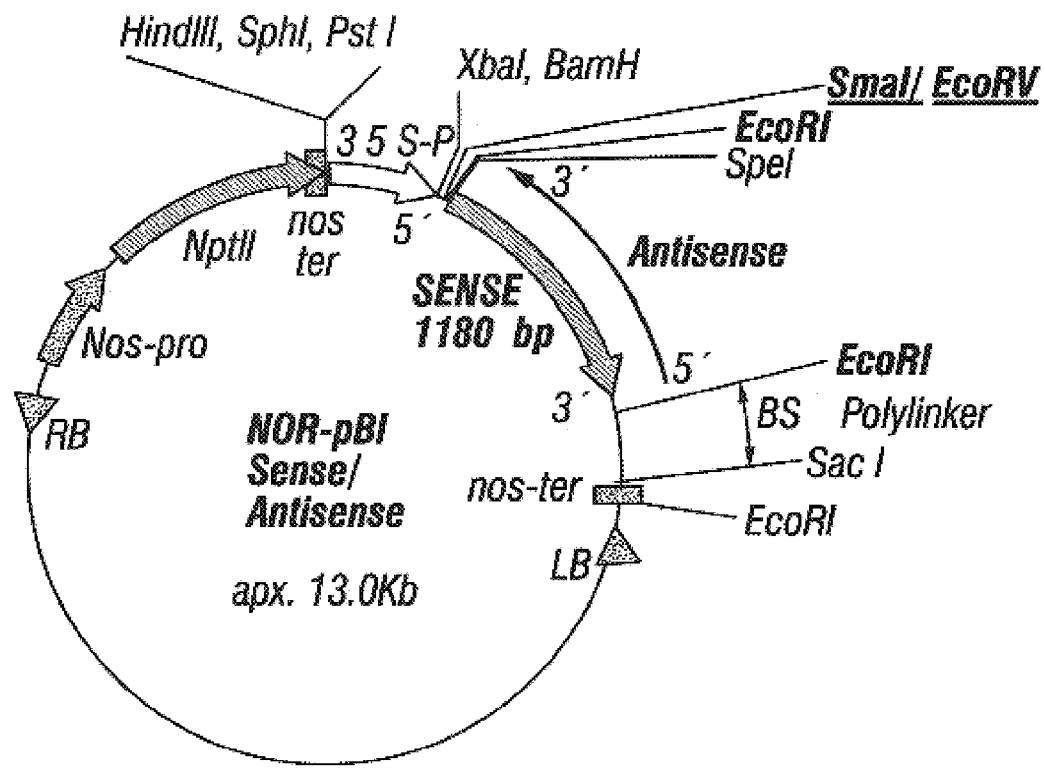
FIG. 1. T-DNA constructs for delivery of sense or antisense NOR gene cDNA (CD-11) sequences into plant genomes. The base plasmid, termed NOR-pBI121 Sense/Antisense (Kanamicin resistant-NPTII), had an approximate size of 13.0 kb. Abbreviations are as follows: FB, LB: right and left T-DNA borders, respectively, Nos-pro: nopaline synthase promoter driving expression of the NPTII gene; NPTII: neomycin phosphotransferase (kanamycin resistance) gene; nos-ter: transaction termination sequence from the nopaline synthase gene; HindIII, SphI, PstI, XbaI, BamHI, SmaI, EcoRI, SpeI, SacI: DNA restriction endonucleases (enzymes); and Sma/EcoRV: the resulting chimeric sequence is recognized by neither enzyme.

The ripening of fleshy fruits represents a system of eukaryotic development unique to plants as well as an important component of agricultural quality and productivity. Greater understanding of the genetic and molecular basis of the ripening process will promote both our collective understanding of plant development and yield tools useful for sustaining and improving agricultural productivity and quality, while minimizing impact on the resources necessary for production. The current invention provides such understanding by providing the nucleic acids encoding the NOR gene. By providing these sequences, the invention provides, for the first time, the ability to use genetic transformation techniques to manipulate a variety of plant characteristics which are associated with these genes in ways that cannot be accomplished via traditional breeding strategies including direct DNA transfer to species other than tomato.

In tomato, ripening occurs over a period of several days, depending on variety, and is characterized by softening, pectin solubilization, increased respiration and ethylene biosynthesis, enhanced pathogen susceptibility, heightened palatability, and accumulation of the characteristic red and orange carotenoid pigments lycopene and beta-carotene, respectively. NOR and also the fruit ripening gene RIN segregate as single traits, result in nearly complete inhibition of normal ripening as defined above, and their effects on ripening cannot be restored via application of exogenous ethylene (Tigchelaar et al., 1978). The ripening phenotypes displayed by RIN and NOR demonstrate that the gene products encoded by the normal alleles at these loci are involved in the primary regulation of ripening (Hobson and Grierson, 1993, Giovannoni 1993; Gray et al., 1994). Because virtually nothing is known of the expression patterns or biochemical nature of the normal NOR gene product, the inventors initiated a genetic map-based cloning strategy for isolation of the corresponding normal allele. All of the prerequisite tools for implementation of this strategy are available in tomato including 1) the mutations themselves, 2) DNA markers tightly linked to both rin and nor, 3) large populations (>300 F2 progeny) segregating for target loci, 4) a library of high molecular weight tomato genomic DNA, and 5) gene transfer technology for verification of cloned target genes via complementation of the recessive phenotype with the dominant allele.

Tomato has served for decades as a model system for both plant genetics and fruit ripening, in part resulting in the availability of the tools for ripening gene isolation mentioned above. Numerous mutations regulating various aspects of tomato fruit ripening have been identified over the years, most of which result in alteration of pigment biosynthesis and/or accumulation without significant effects on additional ripening characteristics (Rick, 1980; Grierson, 1986; Gray et al., 1994). Examples include the greenflesh (gf; Ramirez and Tomes, 1964) and yellowflesh (r; Darby, 1978) mutants which inhibit ripening-related chlorophyll degradation and lycopene accumulation, respectively. Tomato mutations exerting complete or nearly complete inhibition of overall ripening (i.e. blocking changes not just in color but also texture, ethylene biosynthesis, pathogen susceptibility, flavor and aroma) are few, the most extreme being rin and nor.

Neither mutation exerts any observable influence on aspects of plant development or morphology other than ripening, suggesting regulatory roles limited primarily to fruit development (the rin mutation is associated with the mc or macrocalyx phenotype; however, genetic evidence indicates that the rin mutant is actually a double mutant at the linked RIN and MC loci (Robinson and Tomes, 1968)). Fruit homozygous for either rin or nor are similar in phenotype in that they attain full size, produce viable seed, yet remain firm and green for weeks after normal fruit ripen. In addition, homozygous rin and nor mutant fruit fail to display climacteric respiration and ethylene biosynthesis characteristic of normally ripening tomatoes (Tigchelaar et al., 1978), are highly resistant to microbial infection (Grierson, 1986), and are inhibited in their expression of ripening-related genes (DellaPenna et al., 1989; Picton et al., 1993). Although often referred to as recessive mutations, both rin and nor heterozygotes show significant effects on some ripening parameters, including reduced pathogen susceptibility and softening, resulting in extended shelf-life (Tigchelaar et al., 1978; Biggs and Handa, 1989). For this reason, heterozygosity at the RIN locus in particular has seen increased commercial application in fresh market hybrids. Isolation of the RIN and NOR genes by the current inventors permits optimization of controlled ripening via controlled expression in tomato and potentially other fruit crop species. From a broader standpoint, the cloned RIN and NOR genes serve as cornerstones from which to build a model system for analysis of the developmental regulation of fruit ripening control.

I. Rationale and Significance of the Invention

Ripening is a unique and important plant process whose understanding has great significance in the agricultural arts. Isolation of genes regulating both the ethylene and non-ethylene mediated components of fruit ripening represents an important step in understanding the genetic basis of this complex developmental pathway. Although most research emphasis in recent years has been focused on elucidating the biosynthesis and function of ethylene during climacteric fruit ripening, the genetic and molecular basis of the developmental regulators which initiate ripening ethylene biosynthesis, and control the non-ethylene mediated ripening pathway, had remained a mystery. The mutant phenotypes of the targeted nor locus demonstrates that this gene is essential for normal ripening to occur and is a developmental regulator both of ethylene biosynthesis and non-ethylene regulated aspects of ripening. In addition, this gene may be related to those involved in the regulation of other developmental programs. Insights gained into the ripening process as a result of the current invention will not only aid our understanding of overall plant development, but may enhance understanding of developmental processes in other eukaryotes as well.

From the standpoint of agriculture, ripening confers both positive and negative attributes to the resulting commodity. While ripening imparts desirable flavor, color, and texture, considerable expense and crop loss result as a consequence of negative ripening characteristics. For example, ripening related increases in fruit pathogen susceptibility is a major contributor to fruit loss both before and after harvest. This genetically regulated change in fruit physiology currently necessitates the use of pesticides, post-harvest fumigants, and controlled atmosphere storage and shipping mechanisms in attempts to minimize loss. In addition to being wasteful of energy and potentially harmful to the environment, such practices represent major expenses in fruit production.

The current inventors, however, have isolated the ripening regulatory gene NOR, which allows for the first time the genetic enhancement through manipulation of genes of positive ripening attributes and reduction of undesirable qualities in tomato and additional species. The ability to improve fruit quality while reducing energy use, production costs, and environmental impact will promote the long term productivity and sustainability of commercial agriculture.

The current inventors employed a map-based cloning approach for the isolation of the normal NOR locus in tomato. Tomato is the best available system for the map-based cloning of ripening genes because of the availability of: 1) single locus mutations inhibiting normal fruit ripening, 2) a high density RFLP map, 3) large populations segregating for targeted ripening loci, 4) a YAC library, and 5) established procedures for transformation and regeneration. Also, gene products have not been identified for either of the target genes, thus precluding immunological cloning strategies. In addition, previous to the invention one could only speculate concerning patterns of normal NOR gene expression, thus exacerbating the already difficult task of identifying appropriate stages for differential screening strategies. Therefore, the current invention represents a major advance over the prior art, potentially allowing for the first time the creation of transgenic plants having greatly enhanced agronomic characteristics.

II. Alteration of Plant Phenotypes with NOR Nucleic Acid Compositions

(i) NOR Gene Function

The effects and thus potential uses of the NOR (non-ripening) gene can be deduced from analysis of the well characterized mutation at the nor locus (see Tigchellar et al., 1978 and Giovannoni, 1993 for review). Further, the inventors have shown that the NOR gene mutation (nor) greatly inhibits the ripening process with minimal effects on other plant tissues or even fruit prior to the onset of ripening. Consequently, the use of the NOR gene may be indicated for manipulation of fruit ripening. It is also apparent not only from the mutant phenotypes but also from the transgenic expression of the NOR gene (i.e., expression is primarily restricted to the tissues in which effects are observed, fruits) that normal effects are centered on the developing flower, specifically, the carpels (fruit). Nevertheless, manipulation of NOR gene in non-fruit tissues via the tools of biotechnology could be expected to yield various potentially useful effects in non-fruit tissues as well (see examples below). It should be noted that subsequent reference to "normal" and "mutant" refers to the genotypes Nor/Nor and nor/nor, respectively.

Fruit ripening is a complex process ultimately rendering the fruit palatable and/or susceptible to biotic or abiotic process which result in seed liberation and dispersal. While specific ripening attributes vary among species, the following general process are common to many fruits (see Seymour et al., 1993 for review), including tomato, and are all have been shown to be influenced by the NOR gene via characterization of the corresponding mutant:

A) Degradation of the photosynthetic pigment chlorophyll and accumulation of various pigment compounds (often carotenoids and flavonoids) resulting in changes of both color and nutritional composition (Tigchellar et al., 1978; Yen et al., 1997).

B) Changes in cell wall metabolism and architecture resulting in effects on texture and susceptibility to pathogen infection with additional impacts on specific aspects of processing qualities including viscosity and texture of whole and chopped/pureed products (Tigchellar et al., 1978).

C) Changes in carbohydrate metabolism including the conversion of starch to simple sugars (Seymour et al., 1993).

D) Changes in aroma and production of associated volatile compounds.

E) Changes in ethylene hormone biosynthesis and perception (DellaPenna et al., 1989) which directly influence many of the specific ripening attributes mentioned here but may also impact these and other areas via mechanisms not described above. Such processes include effects on pathogen susceptibility, senescence, abscission, seed germination, flowering, sex determination in cucurbits and general stress responses (temperature, drought, mechanical damage) See Ables et al., 1992 for review.

Previous observations, some of which are referenced above, confirm the function of the NOR gene in most aspects of fruit ripening and suggest that additional aspects of plant growth, development and response to the environment could be altered via expression of this gene in other plant tissues via alternate promoters. As such, alteration of any of the forgoing phenotypes, as well as other phenotypes conferred by the NOR gene, as well as plants altered in such ways, specifically form a part of the instant invention.

(ii) Examples of NOR Gene Use.

The NOR gene compositions provided by the inventors may find numerous uses in manipulation of plant phenotypes. Exemplary uses for the NOR gene are described herein below, although those of skill in the art will recognize that the examples are in no way limiting.

1 Control of Fruit Ripening and Quality

Though currently less widely used than the tomato rin (ripening-inhibitor) mutation, the nor mutation is currently used in tomato breeding for development of hybrid lines with slow-ripening/long-shelf-life characteristics. The NOR gene could similarly be used for manipulation and control of ripening with potential for accelerated ripening of important early season crops, controlled or delayed ripening of crops permitting longer shipping handling, storage and post-retail shelf-life. The fact that the inventors have provided the cloned NOR gene will permit its utilization in species other than tomato. Specific examples of use would be in accelerated ripening of early season melons for favorable market position and pricing, and ripening control of bananas and strawberry—fruits which typically have short shelf-lives making shipping and handling more costly.

Next, modified expression of the NOR gene in ripening fruits may find use in elevating levels of important processing and nutritional compounds such as antioxidant flavonoids and carotenoids in fruits and non-fruit tissues. An example would be potential over-expression in maize seeds to enhance accumulation of antioxidant compounds for nutritional enhancement of the crop or for extraction.

Finally, expression of NOR gene orthologues (functional equivalents) in other species may regulate maturation of seed pods (which are also carpels or "fruits", for example in soybean, pea, common bean) and/or cereal grains (e.g., rice, maize, wheat, sorghum). Thus over-expression or repression of the NOR gene may be useful in controlling maturity and maturation time of various cereals. Protracted or accelerated maturation via manipulation of the NOR gene may additionally impact quality characteristics such as total protein content, carbohydrate loading, nutritional composition (e.g., via altered levels of carotenoids such as beta-carotene and lycopene) and total yield.

Figure 2:
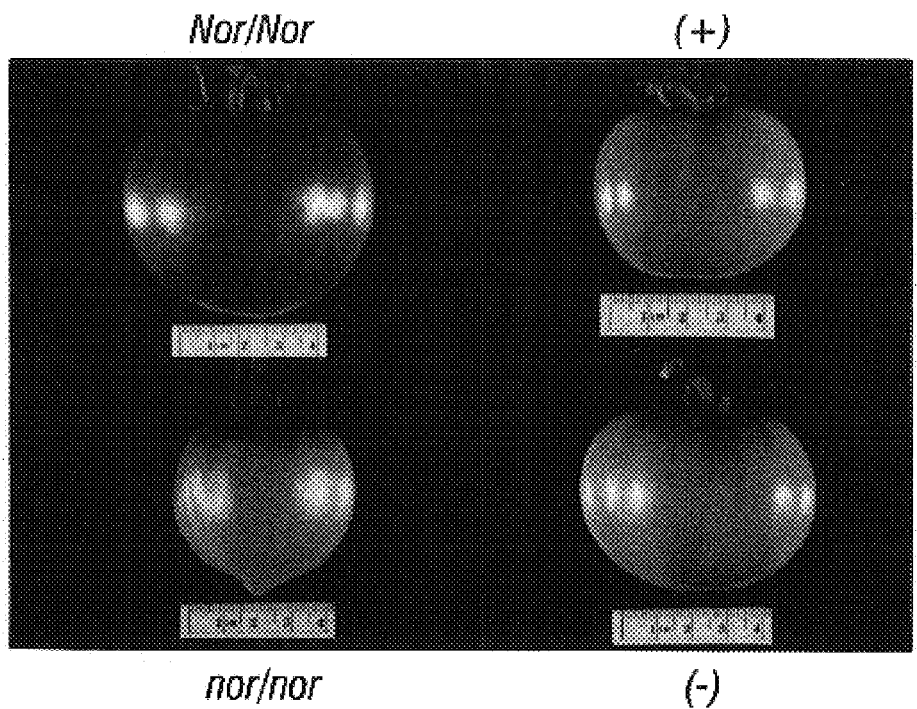
FIG. 2. Manipulation of fruit ripening and carotenoid accumulation with the tomato NOR gene. Shown are representative control and transformed fruit from tomato a line of the genotype nor/nor in the cultivar MHI and transformed with NOR-pBI121 Sense (FIG. 1). Primary transformants (T0) were confirmed for transgene integration via DNA gel-blot analysis and subsequently self-pollinated. Resulting seed were harvested and grown (T1 generation) and analyzed for transgene segregation. Representative fully mature fruit from T1 nor/nor individuals that either harbor the sense NOR transgene (+) or have segregated it out (−) are shown. In summary, transgene expression in the mutant background partially recovers the non-ripening phenotype and confers ripening. In this particular line, relatively low expression of the transgene was observed as compared to expression of NOR in normally ripening (Nor/Nor) fruit. Representative normal (Nor/Nor) and nearly isogenic mutant (nor/nor) cultivar MH1 tomato fruit are shown as controls. The partial recovery of ripening in the nor/nor fruit harboring the NOR-pBI121 (+) transgene verified the isolation of the NOR gene. Furthermore, the partial ripening phenotype observed in this line demonstrated that regulated expression of the NOR gene can be used to create a range of degrees of ripening and ripening-associated characteristics (e.g., carotenoid accumulation, ripe flavor, nutrient composition, softness, pathogen susceptibility).

In support of this example, the inventors have developed T-DNA constructs (FIG. 1) for altering expression of the NOR gene and have transformed such constructs into normal and mutant tomato genotypes. FIG. 2 shows that delivery of the normal Nor allele into the genome of mutant plants results in conversion of fruit from unripe to ripe and results in a range of degrees of ripening and pigment accumulation.

2. Control of Senescence

The NOR gene controls fruit senescence as demonstrated by the lack of senescence in tomato fruits harboring the nor mutation. Senescence or tissue death is thus clearly regulated by NOR in fruit and may be manipulated in non-fruit tissues via regulated expression of the NOR gene. Examples of use may include late fruit-ripening repression in banana or other tropical or sub-tropical fruits subject to rapid decay to permit desirable ripening but not advanced tissue damage reducing fruit quality and desirability. Over-expression in anthers may result in senescence yielding male-sterility, while if this gene is normally expressed in other senescing tissues, gene repression may be useful to inhibit senescence for example in vegetables (spinach, lettuce, cabbage, broccoli).

Studies of the mutant nor phenotype have shown that the nor mutation effects fruit senescence. The inventor's studies comprising the cloning of the NOR gene and development and observation of transgenic tomatoes confirm that the NOR gene confers regulation of fruit ripening and senescence (FIG. 2), and suggest the use of NOR gene nucleic acid compositions for modification of fruit senescence.

3. Control of Pathogen Infection.

Fruit tissue from nor mutant tomato plants are highly resistant to infection by opportunistic microbial pathogens (Tigchellar et al., 1978). Post-ripening repression (antisense or co-suppression) of the gene in tomato, or other species (apple, pear, peach, strawberry, citrus. etc), could thus be useful in inhibiting subsequent over-ripening and pathogen susceptibility of fruit. Along these same lines, activity of the NOR gene may participate in non-fruit pathogen resistance for example via repression of low-level of tissue or cell specific expression in response to pathogen attack. Consequently NOR gene repression may thus be used to provide a positive impact on pathogen resistance in fruit and non-fruit tissues.

4. Control of Ethylene Response

Again, phenotypic studies of fruit ripening effects of the nor mutation and the transgenic complementation studies of the inventor's (FIG. 2) demonstrate that the NOR gene influences both ethylene biosynthesis and response in fruits. As such, NOR can be utilized to manipulate ripening and quality as described above. Nevertheless, ethylene impacts numerous aspects of plant growth and development in addition to ripening, as mentioned and referenced herein above. It is important to note here that inducible over-expression or repression of the NOR gene may be useful in controlling ethylene responses including abscission, senescence, pathogen resistance, germination, and general stress responses (drought, temperature, water, mechanical damage) leading to increased yield and crop performance. Specific examples of use might include 1) synchronized and controlled maturation of cereal grains via high level NOR expression late in seed development, 2) high level expression of NOR later in the growing season to induce senescence and defoliation of cotton via over-expression in leaves prior to boll harvest, and 3) synchronized and accelerated or protracted maturation of seed pods via over-expression or repression, respectively of NOR in soybean. Finally, as stress responses such as responses to pathogen infection, and abiotic stress (temperature, water, mechanical damage) are mediated in part by ethylene, over-expression of the NOR gene may positively impact the ability of plants to withstand biotic and abiotic insults, thus resulting in enhanced crop performance and yield.

5. DNA Markers for Assisted Breeding

The naturally-occurring nor mutation as stated above is already used in breeding of fresh market and processing tomatoes. Current phenotypic selection methods require confirmation of genotype at the nor locus through analysis of fruit development (i.e., the latest stage of plant development) with confirmation requiring analysis of subsequent progeny. Such phenotypic screening requires considerable growth space and 2–3 months per plant generation cycle.

Figure 3:
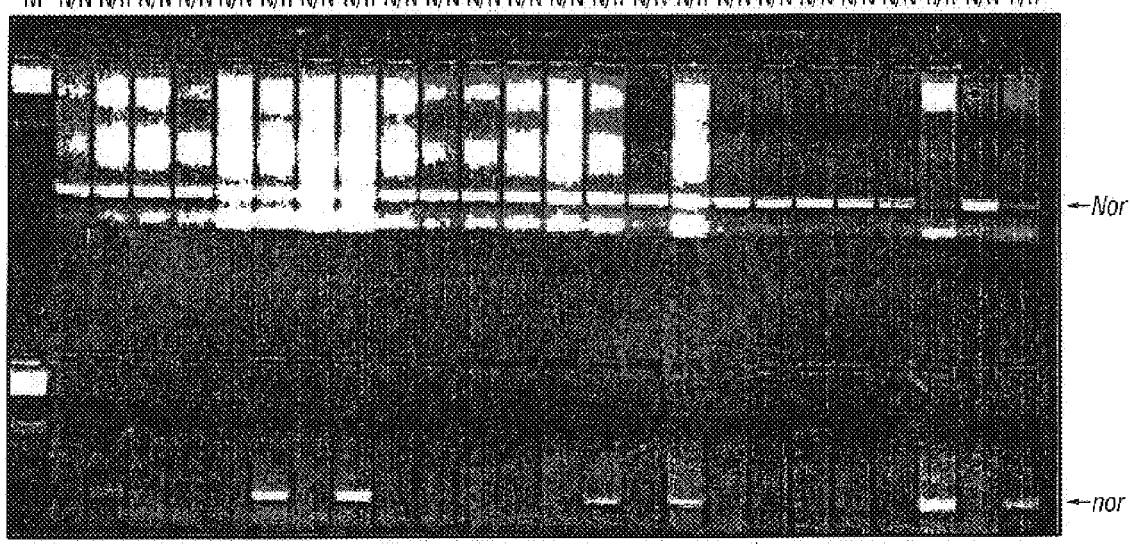
FIG. 3. DNA agarose gel showing the Nor versus nor alleles as PCR amplification products. Genomic DNA was isolated from normal (N/N) and homozygous nor mutant (n/n) nearly isogenic control lines (cultivar MH1), in addition to individuals from a Nor/Nor×Nor/nor back-cross (BC) population. DNA was amplified with one PCR primer common to the coding region of both the Nor and nor alleles and separately with either one primer specific to the Nor or nor alleles, respectively. The allele-specific primers were based on the 2 bp deletion which distinguished the normal (Nor) versus mutant (nor) allele (see FIG. 5). PCR reactions with the normal (Nor) allele primer were loaded on the top portion of the gel, and those employing the mutant (nor) allele primer were loaded on the bottom portion of the gel. PCR reactions from the same individual plant but amplified separately with each allele-specific primer were loaded directly above and below each other to facilitate scoring. The normal (N) and mutant (n) alleles are indicated above each lane and represent the corresponding genotype as determined by analysis of band amplification.

Isolation of the DNA sequences corresponding to the nor mutation has permitted development of DNA markers based on sequence variation between the normal versus mutant tomato genotypes. Use of such markers allows for definitive genotyping of seedlings in a matter of 1–5 days. An example of a DNA marker system based on the nor mutation is shown in FIG. 3. In this example, the 2 bp deletion resulting in the mutation (see below and FIG. 5) is exploited to develop a set of PCR primers which distinguishes the normal versus mutant allele. The sequence variation between the normal versus mutant alleles would be the basis for development of virtually all types of DNA-based markers for determining nor locus genotype through the use of sequences located precisely at (thus 100% accurate) the nor locus.

iii) Summary

Figure 4:
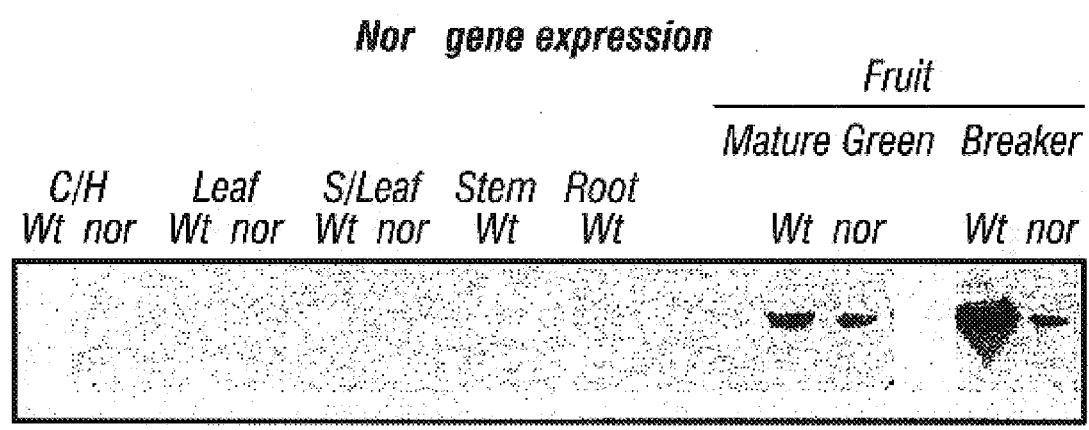
FIG. 4. Expression of the NOR gene through plant development and in normal and mutant fruit. RNA gel-blot analysis of expression using the NOR full-length cDNA as probe. Expression was induced in the transition from mature green to breaker fruit but was not detected in any additional tissues examined including combined cotyledons and hypocotyls (C/H), leaves, senescing leaves (S/Leaf), stems or roots. It was noted that expression was also reduced in identically aged nor (nor/nor) mutant fruit.

The NOR gene cDNA was identified by the inventors and termed CD-11. The gene shows similar transcript size in mutant versus normal fruit (FIG. 4) though it does show reduced accumulation in the mutant. The inventors have also shown that the nor mutation results from a 2 bp deletion in the coding sequence which results in introduction of a premature stop codon through comparative sequencing of the normal versus mutant alleles of the nor locus (FIG. 5). The NOR gene is related to a family of plant transcription factors associated with multiple aspects of plant development including meristem and cotyledon development and leaf senescence (Sour et al., 1996; Aida et al., 1997; John et al., 1997). FIG. 6 depicts the DNA sequence NOR cDNA sequence.

The effects of manipulation of the NOR gene in tomato and other plant species can be readily anticipated via phenotypic observations of the effects of the nor mutation on fruit development. In short, it is likely that most ripening related parameters can be accelerated or inhibited in fruit via over-expression or suppression, respectively of NOR. In addition it is likely that at least a subset of these effects can also be manifested in non-fruit tissues. It would seem particularly likely that ectopic expression of the NOR gene could bring about effects associated with ripening in non-fruit tissues (e.g., senescence, abscission, cell wall alterations and starch conversion, in addition to antioxidant pigment accumulation and associated nutritional enhancement) either directly or in association with other genetic modifications. If processes such as enhanced disease resistance in non-fruit tissues are influenced for example by repression of low level expression of NOR gene, then repression of said gene may have a positive impact on enhancing disease resistance as well.

(iv) Conclusion

An important advance of the instant invention is that it provides novel methods for the modification of plant phenotypes. In particular, by providing the NOR sequence, the invention allows the creation of plants with modified phenotypes. The inventors specifically contemplate the use of the NOR sequence, as well as all of the derivatives thereof which are provided by the invention, to genetically transform plant species for the purpose of altering plant phenotypes. Exemplary phenotypic effects are those which are associated with fruit ripening or ethylene response. In particular, the inventors contemplate increasing the expression of NOR in order to increase fruit ripening and/or ethylene responsiveness, or alternatively, decreasing the effective expression of the NOR gene in order to delay, protract, and/or inhibited fruit ripening or ethylene responses. The expression of NOR sequences in accordance with the invention may be carried out using the native promoter, or alternatively, promoters that are inducible, viral, synthetic, constitutive as described (Poszkowski et al., 1989; Odell et al., 1985), and temporally regulated, spatially regulated (e.g., tissue-specific), and spatio-temporally regulated (Chau et al., 1989).

Types of effects which could be recognized on fruit ripening include, as described in detail above, processes related to changes in color, texture, flavor, aroma, shelf-life, ethylene responses, nutrient composition, cell wall metabolism, and susceptibility to pathogenesis associated with the ripening process. Similarly, effects on ethylene responsiveness which could be effected with the invention include either increased or decreased responsiveness to ethylene. Changes in response to ethylene may effect fruit ripening, organ abscission, seed or pollen dehiscence/shattering, tissue senescence, disease resistance, and response to environmental stresses including but not limited to drought, flooding, heat, cold, nutrient deficiency, high or low light intensity, mechanical damage and insect or pathogen infection. Modification of any of the foregoing effects in a plant, as well as any other effects associated with the NOR gene, is specifically contemplated by the inventors and a part of the current invention.

Potentially any method employing the sequences described by the inventors may be used to realize the above-mentioned phenotypic effects in potentially any plant species, although fruiting effects can be expected to be realized only in species producing fruit. For example, fruit ripening or ethylene responsiveness could be decreased in a given plant by transformation of the plant with an expression vector comprising an antisense NOR gene. Such a NOR gene could comprise the sequences provided herein, or could represent copies of homologous sequences from other plants isolated using the sequences of the invention. Decreases in fruit ripening or ethylene responsiveness could alternatively be realized by use of co-suppression by way of introduction of additional NOR sequences into a host genome. In this case, for example, by introducing multiple exogenous copies of NOR sequences, preferably comprising a functional expression unit, cosuppression of any functional native NOR sequences could be realized, and thereby the phenotype of the plant be modified with respect to traits effected by NOR expression. The effect could be realized potentially by use of the NOR promoter, coding sequences or terminators, or using heterologous versions thereof.

In order to realize the phenotypic effects contemplated by the inventors, it is not required that a particular plant be directly transformed. In particular, once a transgene comprising a sequence of the invention has been introduced into a host plant, that transgene may be passed to any subsequent generation by standard plant breeding protocols. Such breeding can allow the transgene to be introduced into different lines, preferably of an elite agronomic background, or even to different species which can be made sexually compatible with the plant having the transgene. Breeding protocols may be aided by the use of genetic markers which are closely linked to the genes of interest. As such, the instant invention extends to any plant which has been directly introduced with a transgene prepared in accordance with the invention, or which has received the transgene by way of crossing with a plant having such a transgene. The invention may additionally be applied to any plant species. Preferably, a plant prepared in accordance with the invention will be a fruiting plant, for example, tomato, berries such as strawberries and raspberries, banana, kiwi, avocado, melon, mango, papaya, lychee, pear, stone fruits such as peach, apricot, plum and cherry, in addition to true (anatomical) fruits commonly referred to as "vegetables" including peppers, eggplant, okra, and other non-melon curcubuts such as cucumber and squash. Specific examples of other plant species which could be used in accordance with the invention include, but are not limited to, wheat, maize, rye, rice, turfgrass, oat, barley, sorghum, millet, sugarcane, carrot, tobacco, tomato, potato, soybean, canola, sunflower, alfalfa and cotton.

By way of example, one may utilize an expression vector containing a sense or antisense NOR coding region and an appropriate selectable marker to transform a plant cell of a selected species. Any method capable of introducing the expression vector into the cell may be used in accordance with the invention, for example, use of Agrobacterium-mediated DNA transfer, microprojectile bombardment, direct DNA transfer into pollen, by injection of DNA into reproductive organs of a plant, or by direct injection of DNA into the cells of immature embryos followed by the rehydration of desiccated embryos, or by direct DNA uptake by protoplasted cells. The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art. By inclusion of a selectable or screenable marker with an expression vector, those cells receiving the expression vector may efficiently be isolated from those that have not received the vector.

The ultimate goal in the production of transgenic plants having altered phenotypes is to produce plants which are useful to man. In this respect, transgenic plants created in accordance with the current invention may be used for virtually any purpose deemed of value to the grower or to the consumer. For example, the fruit of tomato plants with enhanced fruit ripening characteristics may be harvested and sold to consumers or used in the production of various food products. Additionally, seed could be harvested from the fruit of a plant prepared in accordance with the instant invention, and the seed may be sold to farmers for planting in the field or may be directly used as food, either for animals or humans. Alternatively, products may be made from the seed itself, for example, oil, starch, pharmaceuticals, and various industrial products. Such products may be made from particular plant parts or from the entire plant.

Means for preparing products from plants, such as those that may be made with the current invention, have been well known since the dawn of agriculture and will be known to those of skill in the art. Specific methods for crop utilization may be found in, for example, Sprague and Dudley (1988), and Watson and Ramstad (1987).

III. Plant Transformation Constructs

The construction of vectors which may be employed in conjunction with plant transformation techniques according to the invention will be known to those of skill of the art in light of the present disclosure (see, for example, Sambrook et al., 1989; Gelvin et al., 1990). The techniques of the current invention are thus not limited to any particular nucleic acid sequences in conjunction with the NOR nucleic acid sequences provided herein. Exemplary sequences for use with the invention include those provided in SEQ ID NO: 1, SEQ ID NO:6 and SEQ ID NO:7.

One important use of the sequences of the invention will be in the alteration of plant phenotypes by genetic transformation of plants with sense or antisense NOR genes. The NOR gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the NOR sequences will often depend on the purpose of the transformation. One of the major purposes of transformation of crop plants is to add commercially desirable, agronomically important traits to the plant. Such traits include, but are not limited to, processes related to changes in fruit color, texture, flavor, aroma, shelf-life, ethylene responses, nutrient composition, cell wall metabolism, susceptibility to pathogenesis associated with the ripening process, organ abscission, seed or pollen dehiscence/shattering, tissue senescence, disease resistance, and response to environmental stresses including but not limited to drought, flooding, heat, cold, nutrient deficiency, high or low light intensity, mechanical damage and insect or pathogen infection. In certain embodiments, the present inventors contemplate the transformation of a recipient cell with more than transformation construct. Two or more transgenes can be created in a single transformation event using either distinct selected-gene encoding vectors, or using a single vector incorporating two or more gene coding sequences.

In other embodiments of the invention, it is contemplated that one may wish to employ replication-competent viral vectors for plant transformation. Such vectors include, for example, wheat dwarf virus (WDV) "shuttle" vectors, such as pW1-11 and PW1-GUS (Ugaki et al., 1991). These vectors are capable of autonomous replication in plant cells as well as *E. coli,* and as such may provide increased sensitivity for detecting DNA delivered to transgenic cells. A replicating vector also may be useful for delivery of genes flanked by DNA sequences from transposable elements such as Ac, Ds, or Mu. It also is contemplated that transposable elements would be useful for introducing DNA fragments lacking elements necessary for selection and maintenance of the plasmid vector in bacteria, e.g., antibiotic resistance genes and origins of DNA replication. It also is proposed that use of a transposable element such as Ac, Ds, or Mu would actively promote integration of the desired DNA and hence increase the frequency of stably transformed cells.

It further is contemplated that one may wish to co-transform plants or plant cells with 2 or more vectors. Co-transformation may be achieved using a vector containing the marker and another gene or genes of interest. Alternatively, different vectors, e.g., plasmids, may contain the different genes of interest, and the plasmids may be concurrently delivered to the recipient cells. Using this method, the assumption is made that a certain percentage of cells in which the marker has been introduced, also have received the other gene(s) of interest. Thus, not all cells selected by means of the marker, will express the other genes of interest which had been presented to the cells concurrently.

Vectors used for plant transformation may include, for example, plasmids, cosmids, YACs (yeast artificial chromosomes), BACs (bacterial artificial chromosomes) or any other suitable cloning system. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduced into and have expressed in the host cells. These DNA segments can further include, in addition to a NOR coding sequence, structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

(i) Regulatory Elements

The construction of vectors which may be employed in conjunction with the present invention will be known to those of skill of the art in light of the present disclosure (see e.g., Sambrook et al., 1989; Gelvin et al., 1990). Preferred constructs will generally include a plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang & Russell, 1990), a-tubulin, actin (Wang et al., 1992), cab (Sullivan et al., 1989), PEPCase (Hudspeth & Grula, 1989) or those associated with the R gene complex (Chandler et al., 1989). Tissue specific promoters such as root cell promoters (Conkling et al., 1990) and tissue specific enhancers (Fromm et al., 1989) are also contemplated to be particularly useful, as are inducible promoters such as ABA- and turgor-inducible promoters.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in tomato in particular, will be most preferred.

It is contemplated that vectors for use in accordance with the present invention may be constructed to include the ocs enhancer element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of plant transformation.

It is specifically envisioned that NOR coding sequences may be introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting sense or antisense NOR expression in a tissue-specific manner. For example, these sequences could be targeted to the fruit.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an a-tubulin gene that directs expression in roots.

It also is contemplated that tissue specific expression may be functionally accomplished by introducing a constitutively expressed gene (all tissues) in combination with an antisense gene that is expressed only in those tissues where the gene product is not desired. For example, a gene coding for a NOR sequence may be introduced such that it is expressed in all tissues using the 35S promoter from Cauliflower Mosaic Virus. Expression of an antisense transcript of the same NOR gene in the fruit of a plant would prevent expression of the NOR gene only in the fruit.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

It is contemplated that expression of sense or antisense NOR genes in transgenic plants may in some cases be desired only under specified conditions. It is contemplated that expression of such sequences at high levels may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. A number of genes have been shown to be induced by ABA (Skriver and Mundy, 1990). Therefore, in particular embodiments, inducible expression of the nucleic acid sequences of the invention may be desired.

It also is contemplated by the inventors that in some embodiments of the present invention expression of a NOR gene will be desired only in a certain time period during the development of the plant. Developmental timing is frequently correlated with tissue specific gene expression. For example, expression of certain genes associated with fruit ripening will only be expressed at certain stages of fruit development.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance selectable marker gene, such as the EPSPS gene, to a particular organelle such as the chloroplast rather than to the cytoplasm. This is exemplified by the use of the rbcS transit peptide which confers plastid-specific targeting of proteins. In addition, it is proposed that it may be desirable to target NOR genes to the extracellular spaces or to the vacuole.

It also is contemplated that it may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell.

(ii) Terminators

Transformation constructs prepared in accordance with the invention will typically include a 3' end DNA sequence that acts as a signal to terminate transcription and allow for the poly-adenylation of the mRNA produced by coding sequences operably linked to a NOR gene. In one embodiment of the invention, the native NOR gene is used. Alternatively, a heterologous 3' end may enhance the expression of sense or antisense NOR sequences. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens,* and the 3' end of the protease inhibitor I or II genes from potato or tomato. Regulatory elements such as Adh intron (Callis et al., 1987), sucrose synthase intron (Vasil et al., 1989) or TMV omega element (Gallie et al., 1989), may further be included where desired.

(iii) Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

(iv) Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening'" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

1. Selectable Markers

Many selectable marker coding regions may be used in connection with the NOR sequences of the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan. Where a mutant EPSP synthase is employed, additional benefit may be realized through the incorporation of a suitable chloroplast transit peptide, CTP (U.S. Pat. No. 5,188,642) or OTP (U.S. Pat. No. 5,633,448) and use of a modified maize EPSPS (PCT Application WO 97/04103).

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes.* The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Where one desires to employ a bialaphos resistance gene in the practice of the invention, the inventor has discovered that particularly useful genes for this purpose are the bar or pat genes obtainable from species of Streptomyces (e.g., ATCC No. 21,705). The cloning of the bar gene has been described (Murakami et al., 1986; Thompson et al., 1987) as has the use of the bar gene in the context of plants (De Block et al., 1987; De Block et al., 1989; U.S. Pat. No. 5,550,318).

2. Screenable Markers

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates, a luciferase (lux) gene (Ow et al., 1986), which allows for bioluminescence detection; an aequorin gene (Prasher et al., 1985) which may be employed in calcium-sensitive bioluminescence detection, or a gene encoding for green fluorescent protein (Sheen et al., 1995; Haseloff et al., 1997; Reichel et al., 1996; Tian et al., 1997; WO 97/41228).

Genes from the maize R gene complex can also be used as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively, any genotype of maize can be utilized if the C1 and R alleles are introduced together.

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light. Where use of a screenable marker gene such as lux or GFP is desired, the inventors contemplated that benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding Bt that confers insect resistance on the plant may be introduced into a plant together with a bar gene that is useful as a selectable marker and confers resistance to the herbicide Liberty® on the plant. However, it may not be desirable to have an insect resistant plant that also is resistant to the herbicide Liberty®. It is proposed that one also could introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

It also is contemplated that negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (NPT II) has been investigated as a negative selectable marker in tobacco (*Nicotiana tabacum*) and *Arabidopsis thaliana* (Xiang. and Guerra, 1993). In this example, both sense and antisense NPT II genes are introduced into a plant through transformation and the resultant plants are sensitive to the antibiotic kanamycin. An introduced gene that integrates into the host cell chromosome at the site of the antisense NPT II gene, and inactivates the antisense gene, will make the plant resistant to kanamycin and other aminoglycoside antibiotics. Therefore, rare, site-specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers also may be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, 1993). In the presence of this enzyme the compound 5-fluorocytosine is converted to 5-fluorouracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988).

It also is contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

(iv) Ribozymes

DNA may be introduced into plants for the purpose of expressing RNA transcripts that function to affect plant phenotype yet are not translated into protein. Two examples are antisense RNA, which is discussed in detail below, and RNA with ribozyme activity. Both may serve possible functions in reducing or eliminating expression of native or introduced plant genes, for example, a NOR gene. However, as detailed below, DNA need not be expressed to effect the phenotype of a plant. Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U. S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self splicing introns including Tobacco Ringspot Virus (Prody et al., 1986), Avocado Sunblotch Viroid (Palukaitis et al., 1979), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1994) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

(v) Induction of Gene Silencing

It also is possible that genes may be introduced to produce novel transgenic plants which have reduced expression of a native gene product by the mechanism of co-suppression, thus this technique could be used in accordance with the invention. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

IV. Antisense Constructs

Antisense treatments are one way of altering fruit quality and/or ethylene response and the characteristics associated therewith in accordance with the invention. In particular, constructs comprising the NOR gene in antisense orientation may be used to decrease or effectively eliminate the expression of the gene in a plant. As such, antisense technology may be used to "knock-out" the function of a NOR gene or homologous sequences thereof, thereby causing the delay, protraction or inhibition of fruit ripening and/or decreased ethylene responsiveness, as well as the effects associated therewith.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

V. Methods for Plant Transformation

Suitable methods for plant transformation for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

(i) Agrobacterium-mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), and maize (Ishidia et al., 1996).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

(ii) Electroporation

Where one wishes to introduce DNA by means of electroporation, the method of Krzyzek et al., (U.S. Pat. No. 5,384,253, incorporated herein by reference in its entirety) may be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253, Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

(iii) Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

(iv) Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Fujimara et al., 1985; Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

VI. Site Specific Integration or Excision of Transgenes

It is specifically contemplated by the inventors that one could employ techniques for the site-specific integration or excision of transformation constructs prepared in accordance with the instant invention. Alternatively, site-specific integration techniques could be used to insertionally mutagenize or replace a native NOR gene sequence. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration or excision of transgenes or parts of transgenes can be achieved in plants by means of homologous recombination (see, for example, U.S. Pat. No. 5,527,695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. For example, conserved NOR sequences could be used to replace a native NOR sequence with one of the NOR sequences provided herein. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of approximately $0.5-4.2 \times 10^{-4}$. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of yeast (Golic and Lindquist, 1989), the Gin recombinase of phage Mu (Maeser et al., 1991), the Pin recombinase of E. coli (Enomoto et al., 1983), and the R/RS system of the pSR1 plasmid (Araki et al., 1992). The bacteriophage P1 Cre/lox and the yeast FLP/FRT systems constitute two particularly useful systems for site specific integration or excision of transgenes. In these systems a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

Experiments on the performance of the FLP/FRT system in both maize and rice protoplasts indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule results in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

VII. Biological Functional Equivalents

Modification and changes may be made in the nucleic acids provided by the present invention and accordingly the structure of the polypeptides encoded thereby, and still obtain functional molecules that encode a NOR polypeptide. The following is a discussion based upon alerting nucleic acids in the NOR sequences to result in a changing of the amino acids of a NOR polypeptide to create an equivalent, or even an improved, second-generation molecule. In particular embodiments of the invention, mutated NOR proteins are contemplated to be useful for increasing the activity of the protein. The amino acid changes may be achieved by changing the codons of the DNA sequence, according to the codons given in Table 1.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |

TABLE 1-continued

| Amino Acids | | | Codons | | | | | |
|---|---|---|---|---|---|---|---|---|
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9), and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (+0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine, glutamate and aspartate; serine and threonine, glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of the starting gene product, but with altered and even improved characteristics.

VIII. Production and Characterization of Stably Transformed Plants

After effecting delivery of exogenous DNA to recipient cells, the next steps generally concern identifying the transformed cells for further culturing and plant regeneration. As mentioned herein, in order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

(i) Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) Brassica (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992, U.S. patent application Ser. No. 08/113,561, filed Aug. 25, 1993; U.S. Pat. Nos. 5,508,468; and 5,508,468; each of the disclosures of which is specifically incorporated herein by reference in its entirety).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468, and U.S. patent application Ser. No. 08/604,789.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

(ii) Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. A preferred growth regulator for such purposes is dicamba or 2,4-D. However, other growth regulators may be employed, including NAA, NAA+2,4-D or perhaps even picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g. in an environmentally controlled chamber at about 85% relative humidity, 600 ppm $CO_2$, and 25–250 microeinsteins $m^{-2}$ $s^{-1}$ of light. Plants are preferably matured either in a growth chamber or greenhouse. Plants are regenerated from about. 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Note, however, that seeds on transformed plants may occasionally require embryo rescue due to cessation of seed development and premature senescence of plants. To rescue developing embryos, they are excised from surface-disinfected seeds 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

Progeny may be recovered from transformed plants and tested for expression of the exogenous expressible gene by localized application of an appropriate substrate to plant parts such as leaves. In the case of bar transformed plants, it was found that transformed parental plants ($R_O$) and their progeny of any generation tested exhibited no bialaphos-related necrosis after localized application of the herbicide Basta to leaves, if there was functional PAT activity in the plants as assessed by an in vitro enzymatic assay. All PAT positive progeny tested contained bar, confirming that the presence of the enzyme and the resistance to bialaphos were associated with the transmission through the germline of the marker gene.

(iii) Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

2. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IX. Assays of Transgene Expression

Assays may be employed with the instant invention for determination of the relative efficiency of transgene expression. Such methods would also be useful in evaluating, for example, random or site-specific mutants of the NOR sequences provided herein. Alternatively, assays could be used to determine the efficacy of expression when various different enhancers, terminators or other types of elements potentially used in the preparation of transformation constructs.

For plants, expression assays may comprise a system utilizing embryogenic or non-embryogenic cells, or alternatively, whole plants. An advantage of using cellular assays is that regeneration of large numbers of plants is not required. However, the systems are limited in that promoter activity in the non-regenerated cells may not directly correlate with expression in a plant. Additionally, assays of tissue or developmental specific promoters are generally not feasible.

The biological sample to be assayed may comprise nucleic acids isolated from the cells of any plant material according to standard methodologies (Sambrook et al., 1989). The nucleic acid may be genomic DNA or fractionated or whole cell RNA. Where RNA is used, it may be desired to convert the RNA to a complementary DNA. In one embodiment of the invention, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of protein detected in various transformed plants. Alternatively, clonal cultures of cells, for example, callus or an immature embryo, may be compared to other cells samples.

As indicated, a variety of different assays are contemplated in the screening of cells or plants of the current invention and associated promoters. These techniques may in cases be used to detect for both the presence and expression of the particular genes as well as rearrangements that may have occurred in the gene construct. The techniques include but are not limited to, fluorescent in situ hybridization (FISH), direct DNA sequencing, pulsed field gel electrophoresis (PFGE) analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Quantitation of Gene Expression with Relative Quantitative RT-PCR™

Reverse transcription (RT) of RNA to cDNA followed by relative quantitative PCR™ (RT-PCR™) can be used to determine the relative concentrations of specific mRNA species isolated from plants. By determining that the concentration of a specific mRNA species varies, it is shown that the gene encoding the specific mRNA species is differentially expressed. In this way, a promoters expression profile can be rapidly identified, as can the efficacy with which the promoter directs transgene expression.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ study to successfully determine the relative abundances of a particular mRNA species is that relative concentrations of the amplifiable cDNAs must be normalized to some independent standard. The goal of an RT-PCR™ study is to determine the abundance of a particular mRNA species relative to the average abundance of all mRNA species in the sample.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(ii) Marker Gene Expression

Markers represent an efficient means for assaying the expression of transgenes. Using, for example, a selectable marker, one could quantitatively determine the resistance conferred upon a plant or plant cell by a construct comprising the selectable marker coding region operably linked to the promoter to be assayed, e.g. an RS324 promoter. Alternatively, various plant parts could be exposed to a selective agent and the relative resistance provided in these parts quantified, thereby providing an estimate of the tissue specific expression of the promoter.

Screenable markers constitute another efficient means for quantifying the expression of a given transgene. Potentially any screenable marker could be expressed and the marker gene product quantified, thereby providing an estimate of the efficiency with which the promoter directs expression of the transgene. Quantification can readily be carried out using either visual means, or, for example, a photon counting device.

A preferred screenable marker gene assay for use with the current invention constitutes the use of the screenable marker gene β-glucuronidase (GUS). Detection of GUS activity can be performed histochemically using 5-bromo-4-chloro-3-indolyl glucuronide (X-gluc) as the substrate for the GUS enzyme, yielding a blue precipitate inside of cells containing GUS activity. This assay has been described in detail (Jefferson, 1987). The blue coloration can then be visually scored, and estimates of expression efficiency thereby provided. GUS activity also can be determined by immunoblot analysis or a fluorometric GUS specific activity assay (Jefferson, 1987).

(iii) Purification and Assays of Proteins

One means for determining the efficiency with which a particular transgene is expressed is to purify and quantify a polypeptide expressed by the transgene. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide being assayed always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from-soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

X. Oligonucleotide Probes and Primers

Naturally, the present invention also encompasses DNA segments that are complementary, or essentially complementary, to the sequences set forth in SEQ ID NO: 1, SEQ ID NO:6, and SEQ ID NO:7. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO: 1, SEQ ID NO:6, or SEQ ID NO:7 under relatively stringent conditions such as those described herein. Such sequences may encode the entire NOR protein or functional or non-functional fragments thereof.

Alternatively, the hybridizing segments may be shorter oligonucleotides. Sequences of 17 bases long should occur only once in the genome of most plant species and, therefore, suffice to specify a unique target sequence. Although shorter oligomers are easier to make, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, or 3000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

One method of using probes and primers of the present invention is in the search for genes related to NOR from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

XI. Breeding Plants of the Invention

In addition to direct transformation of a particular genotype with a construct prepared according to the current invention, transgenic plants may be made by crossing a plant having a construct of the invention to a second plant lacking the construct. For example, a nucleic acid sequence encoding a NOR coding sequence can be introduced into a particular plant variety by crossing, without the need for ever directly transforming a plant of that given variety. Therefore, the current invention not only encompasses a plant directly created from cells which have been transformed in accordance with the current invention, but also the progeny of such plants. As used herein the term "progeny" denotes the offspring of any generation of a parent plant prepared in accordance with the instant invention, wherein the progeny comprises a construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:
  (a) plant seeds of the first (starting line) and second (donor plant line that comprises a transgene of the invention) parent plants;
  (b) grow the seeds of the first and second parent plants into plants that bear flowers;
  (c) pollinate a female flower of the first parent plant with the pollen of the second parent plant, and
  (d) harvest seeds produced on the parent plant bearing the female flower.

Backcrossing is herein defined as the process including the steps of:
  (a) crossing a plant of a first genotype containing a desired gene, DNA sequence or element to a plant of a second genotype lacking said desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

XII. Definitions

Genetic Transformation: A process of introducing a DNA sequence or construct (e.g., a vector or expression cassette) into a cell or protoplast in which that exogenous DNA is incorporated into a chromosome or is capable of autonomous replication.

Exogenous gene: A gene which is not normally present in a given host genome in the exogenous gene's present form In this respect, the gene itself may be native to the host genome, however, the exogenous gene will comprise the native gene altered by the addition or deletion of one or more different regulatory elements.

Expression: The combination of intracellular processes, including transcription and translation undergone by a coding DNA molecule such as a structural gene to produce a polypeptide.

Expression vector: A nucleic acid comprising one or more coding sequences which one desires to have expressed in a transgenic organism.

Progeny: Any subsequent generation, including the seeds and plants therefrom, which is derived from a particular parental plant or set of parental plants.

Promoter: A recognition site on a DNA sequence or group of DNA sequences that provide an expression control element for a structural gene and to which RNA polymerase specifically binds and initiates RNA synthesis (transcription) of that gene.

$R_0$ Transgenic Plant: A plant which has been directly transformed with a selected DNA or has been regenerated from a cell or cell cluster which has been transformed with a selected DNA.

Regeneration: The process of growing a plant from a plant cell (e.g., plant protoplast, callus or explant).

Selected DNA: A DNA which one desires to have expressed in a transgenic plant, plant cell or plant part. A selected DNA may be native or foreign to a host genome, but where the selected DNA is present in the host genome, may include one or more regulatory or functional elements which alter the expression profile of the selected gene relative to native copies of the gene.

Selected Gene: A gene which one desires to have expressed in a transgenic plant, plant cell or plant part. A selected gene may be native or foreign to a host genome, but where the selected gene is present in the host genome, will include one or more regulatory or functional elements which differ from native copies of the gene.

Transformation construct: A chimeric DNA molecule which is designed for introduction into a host genome by genetic transformation. Preferred transformation constructs will comprise all of the genetic elements necessary to direct the expression of one or more exogenous genes, for example, NOR genes. Included within in this term are, for example, expression cassettes isolated from a starting vector molecule.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not originally present in a non-transgenic plant of the same strain. The transgenic plant may additionally contain sequences which are native to the plant being transformed, but wherein the "exogenous" gene has been altered in order to alter the level or pattern of expression of the gene.

Transit peptide: A polypeptide sequence which is capable of directing a polypeptide to a particular organelle or other location within a cell.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Genetic Mapping of Fruit Ripening Loci

Three F2 populations, each segregating for one of three ripening mutants, were generated from interspecific crosses between L. esculentum cultivars homozygous for the respective mutant allele and a normally ripening L. cheesmannii parent (accession LA483). As a result RFLP markers less than one cM from both RIN (CT63-0.24 cM) and NOR (CT 16-0.9 cm) were identified.

A) RFLP Mapping of the rin Locus using Pooled DNA Samples: 1840 F2 individuals segregating for the mutant rin allele and RFLP markers were generated from the interspecific cross between L. esculentum homozygous for the mutant rin allele and L. cheesmannii homozygous for the allele conferring the normal ripening phenotype. 45 DNA pools representing a total of 225 mutant individuals (5 plants per pool) were generated from this population. Lanes 1–7 represented a subset of these pools and 35 mutant individuals. Using this subset of DNA pools, the rin locus was initially mapped to a 10 cM region of chromosome 5 flanked by RFLP markers CT93 and TG448. Sample results from gel blot hybridization of pooled DNA samples with RFLP probes are shown for TG448 (tightly linked) and TG185 (unlinked—greater than 50 cM away). "C" represents a DNA pool derived from 5 individuals with ripening fruit. "e" and "c" designate the L. esculentum (mutant) and L. cheesmannii (normal) alleles of the RFLP probes employed, respectively. Hybridization to the "c" allele of TG448 in pools 1, 3 and 6 represents individuals within these pools which have undergone recombination between the TG448 and rin loci. The entire set of 45 pools was used to generate an RFLP map of the rin region of chromosome 5.

B) Generation of linked markers via RAPD analysis of nearly isogenic DNA pools: Methodology for isolating molecular markers linked to targeted regions of the genome is important in the event that markers close enough for initiating a chromosome walk are not available. Until recently, methods for the isolation of molecular markers linked to targeted loci relied upon the availability of nearly isogenic lines (NILs) in which the target locus resides in a highly polymorphic introgressed region (Young et al., 1998, Martin et al., 1991). Although nearly isogenic lines do exist for the rin, nor and Nr loci, in all cases, both the donor and recurrent parents used are L. esculentum cultivars. Unfortunately, extremely low levels of RFLP polymorphism are detected among L. esculentum cultivars (Miller and Tanksley, 1990). Consequently, these NILs are not useful for the identification of new markers linked to ripening loci.

A new strategy was employed that rapidly identifies markers linked to previously mapped target genes for which NILs are not available (Giovannoni et al., 1991). This strategy is based on the generation of nearly isogenic DNA pools from existing RFLP mapping populations. In short, once a target locus has been mapped to a genomic region between flanking RFLP markers, two DNA pools are generated from an RFLP mapping population. Membership in either pool depends on the individuals' parental origin for the target region (as defined by scoring the flanking markers in the RFLP mapping population employed). The result is two DNA pools representing individual progeny selected to be homozygous for loci derived from either one parent or the other across the target region defined by the flanking markers. Since inclusion in a pool is dependent only on the parental origin of the target region, distantly linked and unlinked loci are equally likely to be derived from either parent (i.e. they are not selected for). By combining DNA from multiple individuals into each pool, the chances for homozygosity at loci other than those within the target region becomes minimal. The resulting DNA pools are nearly isogenic for the targeted genomic region. These pools are subsequently utilized as templates for RAPD reactions employing random primer PCR amplification of genomic templates (Williams, et al., 1990). Amplification products which differ between the two nearly isogenic DNA pools are likely to be derived from the target region (Giovannoni et al., 1991).

In order to identify additional markers tightly linked to targeted ripening loci, pairs of DNA pools nearly isogenic for all three ripening locus regions were generated and screened for polymorphic RAPD products. Random primers will be purchased from Operon Technologies and the population used for the generation of isogenic DNA pools is the L. esculentum X L. penneilli F2 mapping population used to generate the tomato RFLP map. This population will be used rather than the actual ripening gene mapping populations because of the higher degree of polymorphism between the parents (Miller and Tanksley, 1990). The purpose of this effort will be to identify tightly linked molecular probes to be utilized in chromosome walks.

In previous analysis employing tomato genomic DNA templates, 3–7 amplification products were detected, on average, per primer. Consequently, 500 primers should result in approximately 2,500 amplified loci of the tomato genome. Given the estimated map size of 1500 cM for the tomato genome, 500 primers should yield approximately 1–2 markers within 1 cM on either side of a target locus. In the event that sufficient polymorphic markers are not identified for one or more of the target loci, additional primers will be acquired through mutual primer exchanges. Also, the use of random primer pairs has recently been demonstrated to yield significant numbers of unique amplification products from tomato genomic DNA.

C) Isolation of a Molecular Marker Linked to the Yin Locus using Isogenic DNA Pools: Linkage analysis permitted the placement of the rin locus between the markers TG503 and TG96. Progeny from an F2 population (L. esculentum X L. pennellii which were scored as homozygous for all markers between CT227 and TG318 were used to target the rin locus. DNA from 7–13 individuals was used to construct 2 nearly isogenic DNA pools. The region shown in black is the resulting chromosome target for the isolation of molecular markers linked to the rin locus. Numbers to the left of the schematic chromosome designates recombination distances in cM between markers designated on the right. A total of 100 random 10 base primers were utilized for amplification of nearly isogenic DNA pools resulting in one polymorphic PCR product, P76. The 0.5 kb P76 amplification product was gel-purified, labeled and mapped via an EcoRI RFLP to the target region.

Example 2

Physical Mapping and Chromosome Walking to $rin^2$

Following identification of DNA markers tightly linked to the RIN locus, physical mapping with high molecular weight DNA gel-blots was performed to assess the feasibility of initiating a chromosome walk. The result was identification of an 800 kb SmaI restriction fragment which hybridized to 3 DNA markers which flanked the RIN locus and span a genetic distance of 4.2 cM. Based on this physical mapping data it was estimated that one cM in the RIN region of chromosome 5 corresponds to approximately 191 kb (800 kb/4.2 cM=191 kb/cM). This estimate is similar to that for the Pto locus which is linked to RIN (Martin el al., 1994).

Given the average 140 kb insert size of the tomato YAC library (Martin et al., 1992), a chromosome walk was initiated from the flanking single copy RFLP markers TG503, and CT93 which are 1.24 cM and 2.9 cM from rin, respectively. CT63, although only 0.24 cM from RIN on the TG503 side, was not employed as a probe because it is a member of a small gene family and unlinked YAC clones would likely be recovered. However, a 360 kb clone (Yrin2) demonstrated hybridization to both TG503 and CT63 suggesting that 1) it contained sequences closer to the target locus than any of the other clones, and 2) the estimated 191 kb/cM ratio in the region of RIN was within two fold of accurate (i.e. TG503 and CT63 are separated by 1 cM and reside on a 360 kb YAC). A single copy end of Yrin2 (Yrin2R) was isolated by inverse PCR and mapped, in a population of 670 F2 progeny, on the RIN side of CT63 0.2 cM from rin. This end was subsequently utilized to take a "step" toward RIN in the tomato YAC library resulting in the isolation of 4 additional YAC clones, Yrin8, Yrin9, Yrin 11, and Yrin12. 7 of the 8 possible YAC ends were isolated through inverse PCR and/or plasmid rescue for generation of a YAC contig via cross-hybridization of ends with RIN region YACs, and RFLP mapping. Two YAC clones were determined to be chimeric based on RFLP mapping (Yrin9R) and sequencing of YAC ends (Yrin8R—greater than 95% homology with tobacco chloroplast DNA). One YAC end, Yrin8L, cosegregated with RIN and hybridized to none of the other YAC clones, suggesting that it extended the furthest toward RIN and may harbor the target gene.

A) Completion of the chromosome walk to RIN: It was demonstrated that an end clone of a RIN region YAC designated Yrin8L cosegregates with RIN in a population of 670 F2 individuals. Based on high stringency (0.2×SSC, 65° C.) DNA gel-blot analysis and RFLP mapping, Yrin8L, is a single copy sequence in the tomato genome. Specific PCR primers were generated which amplify the expected 270 bp fragment of Yrin8L from both the plasmid clone and the tomato genome. The primers were used to PCR screen the tomato YAC library of Martin et al., (1992). Screening of this YAC library via colony hybridization or PCR yielded 1–7 verified (via mapping of end clones and/or cross hybridization to 2 or more probes from the target region) recombinant clones for each of the 6 RIN or NOR linked markers tested. As an alternate strategy, random PstI, EcoRI, or HaeIII subclones of Yrin8 could be employed as probes in the next step toward rin, and the random subclones tested for copy number, map position, and homology to Yrin YACs to ensure sequences from the end of the clone near RIN are used.

B) Isolation and characterization of cDNAs corresponding to genes within YACs containing the target locus: Once candidate RIN containing YAC clones were identified, the clones were used as probes for isolation of cDNAs which may represent transcripts derived from genes contained on the YAC. Two cDNAs were isolated and mapped using Ynor3 as a probe from a "Breaker" fruit cDNA, yielding numerous additional positive clones. Yrin8 also yielded numerous cDNA clones which were tightly linked to the rin locus. A similar strategy was employed by Martin et al. (1993) in identifying the tomato Pto gene on a 400 kb clone from this same library. cDNA libraries in the vector lambda gt 10 and made from Mature Green, Breaker, and Red Ripe stage fruit are all available in the laboratory (lambda gt10 does not cross hybridize with the YAC vector pYAC4). All 3 libraries will be screened because it is not known which stage will express the highest levels of target gene product. Construction of a fourth cDNA library may also be used in lambda gt10 made from mRNA derived from several stages of immature fruit development. Specifically, mRNA will be combined from ovaries prior to pollination, 2 days post pollination, and every 10 days post-pollination up to the Mature Green stage (approximately 30 days in cultivar Ailsa Craig). This library will help to minimize the problem of not knowing when during fruit development the RIN or NOR gene is expressed. Tissue for all but the unpollinated ovaries are stored in a −80° C. freezer.

Example 3

Physical Mapping and Chromosome Walking to NOR

High molecular weight DNA gel-blot analysis was also utilized to estimate the kb/cM ratio in the region of the NOR locus. A 1000 kb CspI fragment hybridized to both CT16 and TG313 which flank the NOR locus and are separated by approximately 5 cM. Based on this observation, it was estimated that 1 cM in the region of the NOR locus corresponds to approximately 200 kb.

Prior to initiation of the chromosome walk to nor, the closest known flanking markers were CT16 (0.9 cM) and CT41 (2.3 cM). Based on the published tomato RFLP map (Tanksley et al., 1992), it was known that TG395 resided in the interval between CT41 and CT16 and thus represented a closer marker to NOR than at least one of the two. TG395 was mapped as a sequence tagged site (due to lack of RFLPs between the two parents of the mapping population) to 1.4 cM from NOR on the CT41 side. PCR screening of the tomato YAC library with TG395 specific primers resulted in the identification of 7 YAC clones ranging in size from 50 kb–490 kb. CT16 was not used for library screening because of difficulty in generating reliable PCR primers.

Three YAC ends were isolated via plasmid rescue and inverse PCR, as described for RIN above. YAC end and RFLP marker cross hybridizations yielded a YAC contig. Of particular interest was the observation that the 470 kb YAC, Ynor3, hybridized to both TG395 (which was used to retrieve this clone from the library) and CT16. Localization of NOR within the interval of chromosome 10 bordered by TG395 and CT16 suggested that the targeted NOR locus resides on Ynor3, and confirmed estimates of kb/cM in this region of the genome. A high titer cosmid library (>500,000 clones) was then prepared of the yeast containing Ynor3 to use in fine mapping and walking to NOR within the Ynor3 clone. The, cosmid vector employed, 04541, contains T-DNA borders to permit direct Agrobacterium transfer into plants. Random Ynor3 PstI and HaeIII subclones were also isolated to use as fine mapping probes. A "breaker" stage tomato fruit cDNA library was also screened with Ynor3 as probe, yielding numerous clones for characterization for linkage to nor.

Example 4

Characterization of YAC Clones Harboring the Rin and Nor Loci

Initial screening with tightly linked RFLP markers yielded 6 YACs linked to the nor locus and 5 YACs linked to rin. Hybridization to YACs with flanking markers revealed that a single nor YAC termed Ynor3 harbored the target gene assuming no internal deletions or other perturbations within the YAC. Similar hybridization experiments, including hybridization with isolated YAC ends, revealed that there were a number of alterations in several of the YACs which presumably occurred during library construction and represented either deletions relative to genomic sequences or chimerism with fragments of genomic DNA derived from unlinked regions of the tomato genome. Extensive characterization of these clones was performed including RFLP mapping of random subclones and YAC ends resulting in determination that the resulting YAC contig did not extend to the point including the rin locus. The terminal YAC end from the YAC extending closest to rin was subsequently used to re-screen the tomato YAC library resulting in identification of 4 additional clones. One of these clones was extensively characterized due to the presence (via hybridization) of DNA markers flanking rin on this single YAC. The results indicated that this particular clone harbored an internal deletion resulting in the absence of the targeted rin locus. Following a third screen of the YAC library using a terminal YAC end from a previous screen as probe, a YAC termed Yrin11 was identified which harbored the rin locus as determined by random subcloning of Yrin11 restriction fragments and RFLP mapping to determine that sequences flanking the target locus were contained on this YAC. This YAC also contained sequences that were absent from the YAC descried above with an internal deletion (thus confirming the integrity of Yrin11), and said fragments were tightly linked to the rin locus.

Example 5 cDNA Library Screening

A 1×amplified breaker fruit cDNA library (cv. Ailsa Craig) in vector lambda TRIPLEX was screened with whole PFGE gel-purified YACs corresponding to Ynor3 and Yrin11, respectively. A contig of tomato BAC clones (library in pBELOBAC11, cultivar LA483—*L. cheesmannii* ) was also simultaneously constructed across the nor region. Similar BAC contig efforts were initiated for the rin region of chromosome 5 but were not completed prior to isolation of the RIN gene. cDNAs hybridizing to the two candidate gene YACs, and thus potentially representing target gene transcripts, were verified for homology via hybridization as probes back to the respective Yrin11 and Ynor3 YACs. Positives were mapped as RFLPs and sequenced.

Example 6

NOR Gene Identification

Ynor3 hybridizing cDNA, CD11, was one of two clones found to cosegregate with the nor locus and to hybridize to the BAC clone most likely (via hybridization to nor-linked markers) to harbor the target locus. Both CD11 and the other co-segregating cDNA (CD5) were hybridized to RNA gel-blots of normal and mutant fruit RNAs. CD5 was constitutively expressed throughout fruit development while CD11 was induced during ripening and by ethylene. CD11 was also greatly reduced in expression in fruit of the nor mutant. CD11 was sequenced and found to have homology to the CUC (cup-shaped-cotyledon) gene of Arabidopsis. This gene also has homology to two functionally defined Arabidopsis transcription factors of otherwise unknown function. Based on CD11 sequence, primers were generated for RT-PCR of CD11 mRNA. CD11 alleles from normal (Nor/ Nor) and mutant (nor/nor) tomato lines were generated by RT-PCR and sequenced. The mutant allele harbors a 2 bp deletion relative to the normal CD11 allele resulting in a stop codon approximately mid-way through the CD11 open reading frame. Based on this mutation, and gene expression patterns described above, in addition to the putative role of CD11 as a transcription factor, it was indicated that the CD11 sequence represents the tomato NOR gene. An original sequence obtained of the clone is indicated in SEQ ID NO: 1 and a corrected version of the sequence in SEQ ID NO:6.

Example 7

Confirmation of NOR Target Gene Isolation

The cDNA identified as representing NOR was be tested for function in ripening through the use of antisense and sense expression constructs in normal and mutant tomatoes, respectively. Antisense gene suppression has proven an effective tool for determining gene function during tomato fruit ripening (reviewed in Gray et al., 1994).

A) Preparation of NOR sense and antisense transformation constructs: T-DNA constructs were prepared for delivery of sense or antisense NOR gene cDNA (CD-11) sequences into plant genomes (FIG. 1). First, NOR-pBI121 sense and antisense constructs were made by replacing the GUS gene of T-DNA binary vector pBI121 with the full-length NOR cDNA referred to as CD-11 (1180 bp) in sense and antisense orientations, respectively, relative to the CaMV35S promoter (35S-P) of pBI121 (FIG. 1). In both constructs, the NOR cDNA (CD11 insert) was subcloned between SmaI and SacI restriction sites resulting from removal of the GUS gene from pBI121. Specifically, EcoRV and SacI sites of the pBluescript vector containing the NOR cDNA were employed due to the fact that SmaI and EcoRV (blunt) ends are compatible for ligation. The resulting ligated sequence no longer can be digested with SmaI or EcoRV. Completed sense and antisense constructs were initially transformed into *E. coli* DH 10B cells and then resulting plasmid DNA was isolated and transformed into *Agrobacterium tumefaciens* strain LBA 4404 for use in transfer into the tomato gene as described herein.

The sense and antisense orientations of the NOR cDNA sequence relative to the EcoRV and SacI restriction sites were obtained by subcloning the original NOR cDNA bound by EcoRI sites from the original cDNA library vector (lambda gt10) into the EcoRI site of plasmid vector pBluescript. Due to the fact that the cDNA sequence was flanked by identical restriction sites (EcoRI), the insert could insert in either direction essentially at random. Several resulting NOR-pBluescript clones were isolated and sequenced to determine the orientation of the cDNA insert relative to the EcoRV and SacI sites of pBluescript, and one clone representing each orientation (sense and antisense) was selected for transfer into the SamI and SacI sites of pBI121 (following removal of the GUS gene from pBI121). In addition to the full-length NOR cDNA 3 bp of pBluescript polylinker (BS) was included on the SmaI side of the cDNA and 51 bp of pBluescript polylinker was included on the SacI side of the insert (including the following restriction sites: SacII, NotI, XbaI, SpeI, BamHI, SmaI, PstI, EcoRI).

A sample of some of the classes of vectors that were prepared by the inventors for studies of the function of the NOR gene is given below, in Table 2.

TABLE 2

Constructs for preparation of RIN and NOR transgenic plants:

| CONSTRUCT | HOST | PURPOSE |
| --- | --- | --- |
| 35s-antisense CD5 | AC wild-type | Phenocopy nor mutation |
| 35s-sense CD5 | AC wild-type | Ectopic expression of nor |
| 35s-sense CD5 | MH1 nor/nor | Complementation of nor mutant/nor confirmation |
| Genomic CD5 | MH1 nor/nor | Complementation of nor mutant/nor confirmation |

B) Transformation of wild type and mutant tomato plants: The sense and antisense NOR constructs prepared as described above were transformed into wild type and nor mutant plants for confirmation of NOR identity. A modified version of the transformation procedure described by Fillattii et al., (1987) was used for generation of transgenic tomato plants (Deikman and Fischer, 1988).

Transgenic tomato plant were prepared as follows. First, the explant was prepared by sterilizing seeds with soaking in 20% bleach+0.1% Tween–20 for 15 minutes. The seeds were rinses 4 times in sterile distilled H2O and the seeds sown on MSO medium ((1 Liter): 4.0 g MS Salts (Gibco), 5.0 ml B5 Vitamins, 5.0 ml MS Iron/EDTA, 20.0 g sucrose, 7.0 g agar (phytagar), pH medium to 6.0 with KOH, autoclave) in sterile glass jars, grow in growth chamber. Agrobacterium was then prepared by streaking selective fresh plates with Agrobacterium containing the desired construct for 2–3 days before it was needed. A single colony was picked from the plate and grown in tubes containing 2 ml YEP medium (YEP Rich Medium (500 ml): 5.0 g Bacto-peptone, 2.5 g NaCl, 5.0 g Bacto Yeast Extract, 7.5 g Bacto agar, autoclave) with appropriate antibiotics, followed by incubation on a shaker at 28° C. overnight. Explants were precultured two days before infection takes place, and 8–10 day old cotyledons were excised. With sterile forceps, cotyledons were removed and placed onto an MSO plate. Using forceps and a blade, the cotyledons were cut in 1–2 pieces. All pieces were then placed on pre-incubation medium ((500 ml): 500 ml MSO Medium, 0.5 ml BAP, 0.1 ml IAA) in a deep petri dish, wrapped in parafilm, and placed in growth chamber for 2 days.

Overnight cultures of Agrobacterium were then precultured and spun down in a 4° C. centrifuge at 2800 rpm for 10 minutes, the supernatant discarded and pellets suspended in 10 ml of induction media ((100 ml): 5 ml AB Salts, 2 ml MES buffer, 2 ml Sodium Phosphate buffer, 91 ml distilled water, 1 g glucose, autoclave, place in 10 tubes, 10 ml each). Then, for co-cultivation, the suspension was added to precultured cotyledon pieces, wrapped in parafilm and shaken gently on roto-shaker for 15 minutes. Using a spatula, cotyledon pieces were placed on co-cultivation media ((500 ml): 500 ml MSO Medium, 1 ml KH2PO4 (100 mg/ml), 250 (1 Kinetin (0.2 mg/ml), 100 (1 2,4 D (1 mg/ml), 735 (1 acetosyringone)), wrapped in parafilm and placed in growth chamber for 2–3 days.

For regeneration, after 2–3 days of being on co-cultivation medium, pieces were transferred to regeneration (2Z) medium ((500 ml): 500 ml MSO Medium, 5.0 ml Carbenicillin stock, 1.0 ml Kanamycin stock, 1.0 ml Zeatin (1 mg/ml), 0.1 ml IAA), wrapped in parafilm and placed in a growth chamber for 2–3 weeks. The tissue was transferred to fresh medium every 2–3 weeks. Generally, calli/shoots were apparent at 6 weeks. The calli was excised from cotyledon tissue and placed on fresh medium. Multiple shoots on one callus were separated and placed on medium, keeping all shoots together on one plate. The taller shoots were placed on deep petri dish. After shoots were well structured, another regeneration (1Z) medium (Regeneration Medium (1Z) (500 ml): 500 ml MSO Medium, 5.0 ml Carbenicillin stock, 1.0 ml Kanamycin stock, 0.5 ml Zeatin (1 mg/ml), 0.1 ml IAA) could be utilized for conserving resources.

When shoots developed a well established meristem, individual shoots were excised of any remaining callus and placed in/on rooting medium ((500 ml): 500 ml MSO medium, 1.0 ml Kanamycin stock, 0.2 ml IAA) in glass jars and placed in a growth chamber. The shoots were watched for signs that: 1. callus continued, therefore suppressing roots to form; in this instance the callus was cut off and again placed on fresh rooting media, or 2. if roots appeared, the plant was ready for soil. Transformed plantlets were then transferred from the glass jar and washed off of any remaining agar on the roots under tap water gently and transplanted in pot filled with moistened soil. The plantlets were watered, making sure soil was thoroughly wet. Plantlets were covered with magenta box to conserve higher humidity. After 5–7 days, the magenta box was gradually removed. Plants were transferred to the greenhouse grown to 10–15 cm.

Media used included the following: YEB Rich Medium (500 ml): 2.75 g Beef Extract, 0.55 g Yeast Extract, 2.75 g peptone, 2.75 g sucrose, 1 ml MgSO4 (1M) pH 7.2, 7.5 g Bactoagar, autoclave. B5 vitamins (100 ml): 2.0 g myo-inositol, 0.2 g thiamine-HCl, 20.0 mg nicotinic acid, 20.0 mg pyridoxine-HCl, mix, then put in autoclaved bottle. MS Iron/EDTA (100 ml): 556.0 mg FeSO4–7H2O, 746.0 mg Na2EDTA-2H2O, mix, then put in autoclaved bottle. Benzylamino-purine (BAP): 1 mg BAP/1 ml H2O, dissolve BAP with 5N KOH dropwise, bring up to volume with ddH2O, filter sterilize in TC Hood, refrigerate. Zeatin: 1 mg Zeatin/1 ml H2O, dissolve with 4N NaOH dropwise, bring up to volume with ddH2O, filter sterilize in TC Hood, refrigerate. Indoleacetic acid (IAA): 1 mg IAA/1 ml ethanol, dissolve with 100% ethanol, filter sterilize in TC Hood, refrigerate in foil (light sensitive, Good 1 week). Acetosyringone stock (ACE) (10 mg/ml): weigh out 100 mg of acetosyringone, add 10 ml 70% ethanol, filter sterilize, put in 1.5 ml tubes, place in −20° C. freezer. Carbenicillin Stock (50 mg/ml): weigh out 5 grams Carbenicillin, add 100 ml ddH2O, filter sterilize, put in 12 ml tubes, place in −20° C. freezer. Kanamycin Stock (50 mg/ml): weigh out 5 grams Kanamycin, add 100 ml ddH2O, filter sterilize, put in 12 ml tubes, place in −20° C. freezer. Tetracycline Stock (3 mg/ml): dissolve 3 mg tetracycline in 1 ml ddH2O, filter sterlize, refrigerate in foil (light sensitive), good 1 day.

The results showed manipulation of fruit ripening and carotenoid accumulation with the tomato NOR gene (FIG. 2). Shown in FIG. 2 are representative control and transformed fruit from tomato a line of the genotype nor/nor in the cultivar MH1 and transformed with NOR-pBI121 Sense (FIG. 1). Primary transformants (T0) were confirmed for transgene integration via DNA gel-blot analysis and subsequently self-pollinated. Resulting seed were harvested and grown (T1 generation) and analyzed for transgene segregation. Representative fully mature fruit from T1 nor/nor individuals that either harbor the sense NOR transgene (+) or have segregated it out (−) are shown. In summary, transgene expression in the mutant background was shown to partially recover the non-ripening phenotype and confer ripening. In this particular line, relatively low expression of the transgene was observed as compared to expression of NOR in normally ripening (Nor/Nor) fruit. Representative normal (Nor/Nor) and nearly isogenic mutant (nor/nor) cultivar MH1 tomato fruit are shown as controls. The partial recovery of ripening in the nor/nor fruit harboring the NOR-pBI121 (+) transgene verified the isolation of the NOR gene. Furthermore, the partial ripening phenotype observed in this line demonstrated that regulated expression of the NOR gene can be used to create a range of degrees of ripening and ripening-associated characteristics (e.g., carotenoid accumulation, ripe flavor, nutrient composition, softness, pathogen susceptibility).

C) Considerations in complementation testing with genomic sequences: Several problems can arise when working with CaMV 35s-cDNA constructs including 1) inappropriate level, developmental timing, or tissue specificity of chimeric gene expression resulting in the absence of a measurable phenotype in antisense or sense plants, and 2) induction of gene expression in inappropriate cell types resulting in malformation or lethality in sense transformants. Because RIN represents a developmental regulator whose activity could potentially prove deleterious to non-fruit tissues, the ideal transgene would be under the control of the normal RIN allele promoter, although other promoters with similar expression profiles could provide similar advantages. Consequently, the major emphasis in verification of putative cDNAs was placed on complementation of the mutant with corresponding genomic counterparts.

Genomic DNA sequences corresponding to the NOR cDNA were isolated from the tomato genomic library whose construction is described below (FIG. 5). Full length cDNAs were sequenced at their termini, and oligonucleotide primers were be synthesized corresponding to the 5' and 3' ends. Candidate genomic clones were then utilized as a template in sequencing reactions with these end primers. Those genomic clones harboring DNA sequences from both ends of the corresponding full length cDNA, as determined by sequencing, were restriction mapped to identify location of the transcribed region within the genomic clone insert. Restriction mapping, in combination with cDNA hybridization to genomic clone fragments, was utilized to identify genomic clones likely to contain at least 2–3 kb of upstream and downstream sequence, prior to transformation. The sequence of the genomic DNA of the NOR gene resulting from the analysis is given in FIG. 5.

D) Construction of target gene containing libraries in the cosmid/plant transformation vector: In order to facilitate generation of a contig spanning a target locus, libraries of genomic DNA from yeast containing YAC clones harboring the desired sequence were constructed using the cosmid/plant transformation vector 04541. The much smaller size of the yeast genome relative to tomato simplified the screening and contig construction. Libraries in 04541 were generated from yeast harboring Yrin8 and Ynor3. Test screening of the Yrin8 library with CT63, Yrin2R, and Yrin8L demonstrated the presence of clones containing all three probed sequences. In addition, clones hybridizing to TG395, CT16, CDnor1 and CDnor2 (the only 4 probes tested) were retrieved from the Ynor3 library as well.

E) Walking in 04541 cosmid libraries from Yrin8L and CDnor2: DNA markers very tightly linked to both RIN (Yrin8L) and NOR (CDnor2) were identified as described. No recombinations were identified between RIN and Yrin8L in 670 F2 progeny, and only one recombinant between NOR and CDnor2 in 347 F2s. Based on the 200 –300 kb/cM estimates for both the RIN and NOR regions of the tomato genome, it was deemed reasonable to attempt a walk to both target loci from these linked markers as they are within the criteria set out for initiating development of a cosmid contig. The walk from CDnor2 was initiated in the Ynor3 yeast cosmid library, while that from Yrin8L was performed in the tomato genomic cosmid library described above because RIN may have been off the end of Yrin8. A DNA sequence surrounding the 04541 cloning site was generated as were nested primers for IPCR of insert ends.

Example 8

Introgression of Transgenes into Elite Crop Varieties

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

Example 9

Marker Assisted Selection

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

In the process of marker assisted breeding, DNA sequences are used to follow desirable agronomic traits (Tanksley et al., 1989) in the process of plant breeding.

Marker assisted breeding may be undertaken as follows. Seed of plants with the desired trait are planted in soil in the greenhouse or in the field. Leaf tissue is harvested from the plant for preparation of DNA at any point in growth at which approximately one gram of leaf tissue can be removed from the plant without compromising the viability of the plant. Genomic DNA is isolated using a procedure modified from Shure et al., (1983). Approximately one gram of leaf tissue from a seedling is lypholyzed overnight in 15 ml polypropylene tubes. Freeze-dried tissue is ground to a powder in the tube using a glass rod. Powdered tissue is mixed thoroughly with 3 ml extraction buffer (7.0 urea, 0.35 M NaCl, 0.05 M Tris-HCl pH 8.0, 0.01 M EDTA, 1% sarcosine). Tissue/buffer homogenate is extracted with 3 ml phenol/chloroform. The aqueous phase is separated by centrifugation, and precipitated twice using $\frac{1}{10}$ volume of 4.4 M ammonium acetate pH 5.2, and an equal volume of isopropanol. The precipitate is washed with 75% ethanol and resuspended in 100–500 $\mu$l TE (0.01 M Tris-HCl, 0.001 M EDTA, pH 8.0).

Genomic DNA is then digested with a 3-fold excess of restriction enzymes, electrophoresed through 0.8% agarose (FMC), and transferred (Southern, 1975) to Nytran (Schleicher and Schuell) using 10×SCP (20 SCP: 2M NaCl, 0.6 M disodium phosphate, 0.02 M disodium EDTA). The filters are prehybridized in 6×SCP, 10% dextran sulfate, 2% sarcosine, and 500 $\mu$g/ml denatured salmon sperm DNA and $^{32}$P-labeled probe generated by random priming (Feinberg & Vogelstein, 1983). Hybridized filters are washed in 2×SCP, 1% SDS at 65° for 30 minutes and visualized by autoradiography using Kodak XAR5 film. Genetic polymorphisms which are genetically linked to traits of interest are thereby used to predict the presence or absence of the traits of interest.

Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and re-probed with a different probe. In this manner one may identify each of the various transgenes that are present in the plant. Further, one of skill in the art will recognize that any type of genetic marker which is polymorphic at the region(s) of interest may be used for the purpose of identifying the relative presence or absence of a trait, and that such information may be used for marker assisted breeding.

Each lane of a Southern blot represents DNA isolated from one plant. Through the use of multiplicity of gene integration events as probes on the same genomic DNA blot, the integration event composition of each plant may be determined. Correlations may be established between the contributions of particular integration events to the phenotype of the plant. Only those plants that contain a desired combination of integration events may be advanced to maturity and used for pollination. DNA probes corresponding to particular transgene integration events are useful markers during the course of plant breeding to identify and combine particular integration events without having to grow the plants and assay the plants for agronomic performance.

It is expected that one or more restriction enzymes will be used to digest genomic DNA, either singly or in combinations. One of skill in the art will recognize that many different restriction enzymes will be useful and the choice of restriction enzyme will depend on the DNA sequence of the transgene integration event that is used as a probe and the DNA sequences in the genome surrounding the transgene. For a probe, one will want to use DNA or RNA sequences which will hybridize to the DNA used for transformation. One will select a restriction enzyme that produces a DNA fragment following hybridization that is identifiable as the transgene integration event. Thus, particularly useful restriction enzymes will be those which reveal polymorphisms that are genetically linked to specific transgenes or traits of interest.

Example 10

General Methods for Assays

DNA analysis of transformed plants is performed as follows. Genomic DNA is isolated using a procedure modified from Shure, et al., 1983. Approximately 1 gm callus or leaf tissue is ground to a fine powder in liquid nitrogen using a mortar and pestle. Powdered tissue is mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate is extracted with 4 ml phenol chloroform. The aqueous phase is separated by centrifugation, passed through Miracloth, and precipitated twice using $\frac{1}{10}$ volume of 4.4 M ammonium acetate, pH 5.2 and an equal volume of isopropanol. The precipitate is washed with 70% ethanol and resuspended in 200–500 $\mu$l TE (0.01 M Tris-HCl, 0.001 M EDTA, pH 8.0).

The presence of a DNA sequence in a transformed cell may be detected through the use of polymerase chain reaction (PCR). Using this technique specific fragments of DNA can be amplified and detected following agarose gel electrophoresis. For example, two hundred to 1000 ng genomic DNA is added to a reaction mix containing 10 mM Tris-HCl pH 8.3, 1.5 mM $MgCl_2$, 50 mM KCl, 0.1 mg/ml gelatin, 200 $\mu$M each dATP, dCTP, dGTP, dTTP, 0.5 $\mu$M each forward and reverse DNA primers, 20% glycerol, and 2.5 units Taq DNA polymerase. The reaction is run in a thermal cycling machine as follows: 3 minutes at 94° C., 39 repeats of the cycle 1 minute at 94° C., 1 minute at 50° C., 30 seconds at 72° C., followed by 5 minutes at 72° C. Twenty $\mu$l of each reaction mix is run on a 3.5% NuSieve gel in TBE buffer (90 mM Tris-borate, 2 mM EDTA) at 50V for two to four hours.

For Southern blot analysis genomic DNA is digested with a 3-fold excess of restriction enzymes, electrophoresed through 0.8% agarose (FMC), and transferred (Southern, 1975) to Nytran (Schleicher and Schuell) using 10×SCP (20×SCP: 2 M NaCl, 0.6 M disodium phosphate, 0.02 M disodium EDTA). Probes are labeled with $^{32}$p using the random priming method (Boehringer Mannheim) and purified using Quik-Sep® spin columns (Isolab Inc., Akron, Ohio). Filters are prehybridized at 65° C. in 6×SCP, 10% dextran sulfate, 2% sarcosine, and 500 $\mu$g/ml heparin (Chomet et al., 1987) for 15 min. Filters then are hybridized overnight at 65 C. in 6×SCP containing 100 $\mu$g/ml denatured salmon sperm DNA and $^{32}$P-labeled probe. Filters are washed in 2×SCP, 1% SDS at 65 C. for 30 min. and visualized by autoradiography using Kodak XAR5 film. For rehybridization, the filters are boiled for 10 min. in distilled $H_2O$ to remove the first probe and then prehybridized as described above.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

Abdullah et al., *Biotechnology*, 4:1087, 1986.
Abel et al., *Science*, 232:738–743, 1986.
Abeles F, Morgan P and Saltveit M (1992) Ethylene in Plant Biology (San Diego: Academic Press)
Abeles F. Morgan P and Saltveit M (1992) Ethylene in Plant Biology (San Diego: Academic Press)
Aida M, Ishida T, Fukaki H, Fujisawa H, and Tasaka M. (1997) Genes involved in organ separation in arabidopsis: An analysis of the cup-shaped cotyledon mutant. Plant Cell. 9: 841–857.
Anteguera, F., Bird, A. (1989) Unmethylated CpG islands associated with genes in higher plant DNA. The EMBO J. 7:2295–2299.
Araki et al., *J. Mol. Biol.* 225(1):25–37, 1992.
Armaleo et al., *Curr. Genet.* 17(2):97–103, 1990.
Armstrong et al., *Maize Genetics Coop Newsletter*, 65:92–93, 1991.
Baile, J. and Young, R. (1981) Respiration and ripening in fruits-retrospect and prospect. In Recent Advances in the Biochemistry of Fruits and Vegetables. Friend, J. and Rhodes, M. (ads.). Academic Press. pp 1–39.
Bansal et al., *Proc. Nat'l Acad. Sci. USA*, 89:3654–3658, 1992.
Barkai-Golan et al., *Arch. Microbiol.*, 116:119–124, 1978.
Bates, *Mol. Biotechnol.*, 2(2):135–145, 1994.
Battraw and Hall, *Theor. App. Genet.*, 82(2):161–168, 1991.
Belanger and Kriz, *Genet.*, 129:863–872, 1991.
Bellus, *J. Macromol. Sci. Pure Appl. Chem.*, RS3241(1):1355–1376, 1994.
Benfey, Ren, Chua, *EMBO J.*, 8:2195–2202, 1989.
Bernal-Lugo and Leopold, *Plant Physiol.*, 98:1207–1210, 1992.
Berzal-Herranz et al., *Genes and Devel.*, 6:129–134, 1992.
Bevan et al., *Nucleic Acids Research*, 11(2):369–385, 1983.
Bhattacharjee; An; Gupta, *J. Plant Bioch. and Biotech.* 6, (2):69–73. 1997.
Biggs, M. and Handa, A. (1989) Temporal regulation of polygalacturonase gene expression in fruits of normal, mutant, and heterozygous tomato genotypes. Plant Physiol. 89:117–125.
Blackman et al., *Plant Physiol.*, 100:225–230, 1992.
Bol et al., *Annu. Rev. Phytopath.*, 28:113–138, 1990.
Bouchez et al., *EMBO Journal*, 8(13):4197–4204, 1989.
Bower et al., *The Plant Journal*, 2:409–416. 1992.
Bowler et al., *Ann Rev. Plant Physiol.*, 43:83–116, 1992.
Branson and Guss, *Proceedings North Central Branch Entomological Society of America*, 27:91–95, 1972.
Broakaert et al., *Science*, 245:1100–1102, 1989.
Buchanan-Wollaston et al., *Plant Cell Reports* 11:627–631. 1992

Buising and Benbow, *Mol Gen Genet*, 243(1):71–81. 1994.
Burke, D., Carle, G. and Olson, M. (1987) Cloning of large segments of exogenous DNA into yeast by means of artificial chromosome vectors. Science. 236:806–812.
Callis, Fromm, Walbot, *Genes Dev.*, 1:1183–1200, 1987.
Campbell (ed.), In: *Avermectin and Abamectin*, 1989.
Capaldi et al., *Biochem. Biophys. Res. Comm.*, 76:425, 1977.
Casa et al., *Proc. Nat'l Acad. Sci. USA*, 90(23):11212–11216, 1993.
Cashmore et al., *Gen. Eng. of Plants*, Plenum Press, New York, 29–38, 1983.
Cech et al., *Cell*, 27:487–496, 1981.
Chandler et al., *The Plant Cell*, 1:1175–1183, 1989.
Chau et al., *Science*, 244:174–181, 1989.
Chomet et al., *EMBO J.*, 6:295–302, 1987.
Chowrira et al., *J. Biol. Chem.*, 269:16096–25864, 1994.
Christou; Murphy; Swain, *Proc. Nat'l Acad. Sci. USA*, 84(12):3962–3966, 1987.
Chu et al., *Scientia Sinica*, 18:659–668, 1975.
Coe et al., In: *Corn and Corn Improvement*, 81–258, 1988.
Conkling et al., *Plant Physiol.*, 93:1203–1211, 1990.
Cordero, Raventos, San Segundo, *Plant J.*, 6(2)141–150, 1994.
Cordes, S., Deikman, J., Margossian, L. and Fischer, R. (1989) Interaction of a developmentally regulated DNA-binding factor with sites flanking two different fruit-ripening genes from tomato. The Plant Cell. 1:1025–1034.
Coxson et al., *Biotropica*, 24:121–133, 1992.
Cretin and Puigdomenech, *Plant Mol. Biol.* 15(5):783–785, 1990.
Cuozzo et al., *Bio/Technology*, 6:549–553, 1988.
Cutler et al., *J. Plant Physiol.*, 135:351–354, 1989.
Czapla and Lang, *J. Econ. Entomol.*, 83:2480–2485, 1990.
Davies et al., *Plant Physiol.*, 93:588–595, 1990.
De Block et al., *The EMBO Journal*, 6(9):2513–2518, 1987.
De Block, De Brouwer, Tenning, *Plant Physiol.*, 91:694–701, 1989.
DellaPenna, D. and Giovannoni, J. (1991) Regulation of gene expression in ripening tomatoes. In Developmental Regulation of Plant Gene Expression Vol.2. Grierson, D. (ed.). Blackie and Son Ltd. pp182–216.
DellaPenna, D., Alexander, D. and Bennett, A. (1986) Molecular cloning of tomato fruit polygalacturonase: Analysis of polygalacturonase mRNA levels during ripening. PNAS USA. 83:6420–6424.
DellaPenna, D., Lincoln, J., Fischer, R. and Bennett, A. (1989) Transcriptional analysis of polygalacturonase and other ripening associated genes in Rutgers, rin, nor, and Nr tomato fruit. Plant Physiol. 90:1372–1377.
Dellaporta et al., In: *Chromosome Structure and Function: Impact of New Concepts*, 18th Stadler Genetics Symposium, 11:263–282, 1988.
Dennis et al., *Nucl. Acids Res.*, 12(9):3983–4000, 1984.
Depicker et al., *Plant Cell Reports*, 7:63–66, 1988.
D'Halluin et al., *Plant Cell*, 4(12):1495–1505, 1992.
Didierjean et al., *Plant Mol Biol* 18(4):847–849, 1992.
Dure et al., *Plant Molecular Biology*, 12:475–486, 1989.
Ebert et al., 84:5745–5749, *Proc. Nat'l Acad. Sci. USA*, 1987.
Ellis et al., *EMBO Journal*, 6(11):3203–3208, 1987.
Enomoto, et al., *J. Bacteriol.*, 6(2):663–668, 1983.
Erdmann et al., *Mol. Jour. Gen. Micro.*, 138:363–368, 1992.
Feinberg and Vogelstein, *Anal Biochem.*, 132:6–13, 1983.
Finkle et al., *Plant Sci.*, 42:133–140, 1985.
Fischer, R. and Bennett, A. (1991) Role of cell wall hydrolases in fruit ripening. Ann. Rev. Plant. Physiol. Plant Molec. Biol. 42:

Fitzpatrick, *Gen. Engineering News*, 22:7, 1993.
Forster and Symons, *Cell*, 49:211–220, 1987.
Fraley et al., *Bio/Technology*, 3:629–635, 1985.
Franken et al., *EMBO J.*, 10(9):2605–2612, 1991.
Fransz, de Ruijter, Schel, *Plant Cell Reports*, 8:67–70, 1989.
Fromm et al., *Nature*, 312:791–793, 1986.
Gailie et al., *The Plant Cell*, 1:301–311, 1989.
Ganal, M. and Tanksley, S. (1989) Analysis of tomato DNA by pulsed field gel electrophoresis. Plant Mol. Biol. Rep. 7:17–27.
Ganal, M., Martin, G., Messeguer, R. and Tanksley, S. (1990) Application of RFLPs, physical mapping, and large DNA technologies to the cloning of important genes from crop plants. AgBiotech News and Info. 2:835–840.
Ganal, M., Young, N. and Tanksley, S. (1989) Pulsed field gel electrophoresis and physical mapping of large DNA fragments in the Tm-2a region of chromosome 9 in tomato. Mol. Gen. Genet. 215:395–400.
Gatehouse et al., *J. Sci. Food. Agric.*, 35:373–380, 1984.
Gelvin et al., In: *Plant Molecular Biology Manual*, 1990.
Gerlach et al., *Nature* 328:802–805, 1987.
Ghosh-Biswas, Iglesias, Datta, Potrykus, *J. Biotechnol.*, 32(1): 1–10, 1994.
Giovannoni, J. (1993) Molecular biology of fruit development and ripening. In *Methods In Plant Molecular Biology*. (Bryant, J. ed.) Academic Press. Vol. 10: 253–287.
Giovannoni, J., DellaPenna, D., Bennett, A. and Fischer, R. (1989) Expression of a chimeric polygalacturonase gene in transgenic rin (ripening inhibitor) tomato fruit results in polyuronide degradation but not fruit softening. The Plant Cell. 1:53–63.
Giovannoni, J., DellaPenna, D., Bennett, A. and Fischer, R. (1991) Polygalacturonase and tomato fruit ripening. Horticultural Reviews. 13:67–103.
Giovannoni, J., Noensie, E., Ruezinsky, D., Lu, X, Tracy, S., Ganal, M., Martin, G., Pillen, K. and Tanksley, S. (1995) Molecular genetic analysis of the ripening-inhibitor and non-ripening loci of tomato: a first step in genetic map-based cloning of fruit ripening genes. Molecular and General Genetics 248(2): 195–206.
Giovannoni, J., Wing, R., Ganal, M. and Tanksley, S. (1991) Isolation of molecular markers from specific chromosomal intervals using DNA pools from existing mapping populations. Nuc. Acids Res. 19:6553–6558.
Golic and Lindquist, *Cell*, 59:3, 499–509. 1989.
Gomez et al., *Nature* 334:262–264. 1988.
Goring et al., *Proc. Nat'l Acad Sci. USA*, 88:1770–1774, 1991.
Grierson, D. (1986) Molecular biology of fruit ripening. In Oxford Surveys of Plant Molecular and Cell Biology Vol.3 . Milan, B (ad.). Oxford University Press. pp363–383.
Grierson, D., Tucker, G., Keen, J., Ray, J., Bird, C. and Schuch, W. (1986). Sequencing and identification of a cDNA clone for tomato polygalacturonase. Nuc. Acids Res. 1 4:8595–8603.
Guerrero et al., *Plant Molecular Biology*, 15:11–26, 1990.
Gupta et al., *Proc. Nat'l Acad. Sci. USA*, 90:1629–1633, 1993.
Hagio, Blowers, Earle, *Plant Cell Rep.*, 10(5):260–264, 1991.
Hamilton et al., *Proc. Nat'l Acad. Sci. USA*, 93(18): 9975–9979, 1996.
Hamilton, A., Lycett, G. and Grierson, D. (1990) Antisense gene that inhibits synthesis of the hormone ethylene in transgenic plants. Nature. 346:284–287.
Hammock et al., *Nature*, 344:458–461, 1990.
Harriman, R. and Handa, A. (1991) Molecular cloning of tomato pectin methylesterase gene and its expression in Rutgers, ripening inhibitor, nonripening and Never ripe tomato fruits. Plant Physiol. 97:
Haseloff and Gerlach, *Nature*, 334:585–591, 1988.
Haseloff et al., *Proc. Nat'l Acad. Sci. USA* 94(6):2122–2127, 1997.
He et al., *Plant Cell Reports*, 14 (2–3):192–196, 1994.
Hemenway et al., *The EMBO J.*, 7: 1273–1280, 1988.
Henikoff, S. (1984) Unidirectional digestion with exonuclease lit creates targeted breakpoints for DNA sequencing. Gene. 28:351–359.
Hensgens et al, *Plant Mol. Biol.*, 22(6):1101–1127, 1993.
Hiei et al., *Plant. Mol. Biol.*, 35(1–2):205–218, 1997.
Hilder et al., *Nature*, 330:160–163, 1987.
Hinchee et al., *Bio/technol.*, 6:915–922, 1988.
Hobson, G. (1968) Cellulase activity during the maturation and ripening of tomato fruit. J. Food Sci. 33:588–592.
Hou and Lin, *Plant Physiology*, 111:166, 1996.
Hudspeth and Grula, *Plant Mol. Biol.*, 12:579–589, 1989.
Ikeda et al., *J. Bacteriol.*, 169:5615–5621, 1987.
Ikuta et al., *Bio/technol.*, 8:241–242, 1990.
Ishida et al., *Nat. Biotechnol.*, 14(6):745–750, 1996.
Jefferson R. A., *Plant Mol. Biol. Rep.*, 5:387–405, 1987.
John I, Hackett R, Cooper W, Drake R, Farrell A, and Grierson D. Cloning and characterization of tomato leaf senescence-related cDNAs. Plant Molecular Biology. 33: 641–651.
Johnson et al., *Proc. Nat'l Acad. Sci. USA*, 86:9871–9875, 1989.
Joshi, *Nucleic Acids Res.*, 15:6643–6653, 1987.
Joyce, *Nature*, 338:217–244, 1989.
Kaasen et al., *J. Bacteriology*, 174:889–898, 1992.
Kaeppler et al., *Plant Cell Reports* 9: 415–418, 1990.
Kaeppler, Somers, Rines, Cockburn, *Theor. Appl. Genet.*, 84(5–6):560–566, 1992.
Karsten et al., *Botanica Marina*, 35:11–19, 1992.
Katz et al., *J. Gen. Microbiol.*, 129:2703–2714, 1983.
Keller et al., *EMBO J.*, 8(5):1309–1314, 1989.
Kim and Cech, *Proc. Nat'l Acad. Sci. USA*, 84:8788–8792, 1987.
Kinzer, S., Schwager, S. and Mutschler, M. (1990) Mapping of ripening-related or -specific cDNA clones of tomato. Theor. Appl. Genet. 79:489–496.
Klee, Yanofsky, Nester, *Bio-Technology*, 3(7):637–642, 1985.
Knittel, Gruber; Hahne; Lenee, *Plant Cell Reports*, 14(2–3): 81–86, 1994.
Kohler et al., *Plant Mol. Biol.*, 29(6):1293–1298, 1995.
Koster and Leopold, *Plant Physiol.*, 88:829–832, 1988.
Kramer, M., Sanders, R., Sheehy, R., Melis, M., Kuehn, M. and Hiatt, W. (1990) Field evaluation of tomatoes with reduced polygalacturonase by antisense RNA. In Horticultural Biotechnology. Bennett, A. and O'Neill, S. (eds.) Alan R. Liss. pp347–355.
Kriz, Boston, Larkins, *Mol. Gen. Genet.*, 207(1):90–98, 1987.
Kunkel et al., *Methods Enzymol.*, 154:367–382, 1987.
Langridge and Feix, *Cell*, 34:1015–1022, 1983.
Langridge et al., *Proc. Nat'l Acad. Sci. USA*, 86:3219–3223, 1989.
Laufs et al., *Proc. Nat'l Acad. Sci.*, 7752–7756, 1990.
Lawton et al., *Plant Mol. Biol.* 9:315–324, 1987.
Lazzeri, *Methods Mol. Biol.*, 49:95–106, 1995.
Lee and Saier, *J. of Bacteriol.*, 153–685, 1983.
Lee, Suh; Lee, *Korean J. Genet.*, 11(2):65–72, 1989.
Levings, *Science*, 250:942–947, 1990.

Lieber and Strauss, *Mol. Cell. Biol.*, 15: 540–551, 1995.

Lincoln, J. and Fischer, R. (1988) Regulation of gene expression by ethylene in wild-type and rin tomato (*Lycopersicon esculentum* ) fruit. Plant Physiol. 88:370–374.

Lincoln, J., Cordes, S., Read, E. and Fischer, R. (1987) Regulation of gene expression by ethylene during *Lycopersicon esculentum* (tomato) fruit development. PNAS USA. 84: 2793–2797.

Lindstrom et al., *Developmental Genetics,* 11:160, 1990.

Loomis et al., *J. Expt. Zoology,* 252:9–15, 1989.

Lorz et al., *Mol. Gen Genet,* 199:178–182, 1985.

Ma et al., *Nature,* 334:631–633, 1988.

Maeser et al., *Mol. Gen. Genet.,* 230(1–2):170–176, 1991.

Marcotte et al., *Nature,* 335:454, 1988.

Margossian, L., Federman, A., Giovannoni, J. and Fischer, R. (1988) Ethylene-regulated expression of a tomato fruit ripening gene encoding a proteinase inhibitor I with a glutamic residue at the reactve site. PNAS USA. 85:8012–8016.

Mariani et al., *Nature,* 347:737–741, 1990.

Martin, G., Ganal, M. and Tanksley, S. (1992) Construction of a yeast artificial chromosome library of tomato and identification of clones linked to two disease resistance loci. Mol. Gen. Genet In press.

Martinez, Martin, Cerff, *J. Mol. Biol.,* 208(4):551–565, 1989.

Maunders, M., Holdsworth, M., Slater, A., Knapp, J., Bird, C., Schuch, W. and Grierson, D. (1987) Ethylene stimulates the accumulation of ripening-related mRNAs in tomatoes. Plant Cell Environ. 10:177–184.

McCabe, Martinell, *Bio-Technology,* 11(5):596–598, 1993.

McCormac et al., *Euphytica,* v. 99 (1) p. 17–25, 1998.

McCormick, S., Neidermeyer, J., Fry, J., Barnason, A., Horsch, R. and Frayley, R. (1986) Leaf disk transformation of cultivated tomato (*Lycopersicon esculentum*) using *Agrobacterium tumefaciens.* Plant Cell Rep. 5:81–84.

McElroy et al., *Mol. Gen. Genet.,* 231:150–160, 1991.

McElroy, Zhang, Cao, Wu, *Plant Cell,* 2:163–171, 1990.

Meagher, *Int. Rev. Cytol.,* 125 :139–163, 1991.

Messeguer, R., Ganal, M., deVicente, M., Young, N., Bolkan, H. and Tanksley, S. (1991) Characterization of the level, target sites and inheritance of cytosine methylation in tomato nuclear DNA. Plant Mol. Biol.

Michel and Westhof, *J. Mol. Biol.,* 216:585–610, 1990.

Miller, J. and Tanksley, S. (1990)RFLP analysis of phylogenetic relationships and genetic variation in the genus *Lycopersicon.* Theor. Appl. Genet. 80:437–448.

Mundy and Chua, *The EMBO J.,* 7:2279–2286, 1988.

Murakami et al., *Mol. Gen. Genet.,* 205:42–50, 1986.

Murashige and Skoog, *Physiol. Plant.,* 15:473–497, 1962.

Murdock et al., *Phytochemistry,* 29:85–89, 1990.

Nagatani, Honda, Shimada, Kobayashi, *Biotech. Tech.,* 11(7):471–473, 1997.

Napoli, Lemieux, Jorgensen, *Plant Cell,* 2:279–289, 1990.

Odell et al., *Nature,* 313:810–812, 1985.

Oeller, P., Min-Wong, L., Taylor, L., Pike, D. and Theologis, A. (1991) Reversible inhibition of tomato fruit senescence by antisense RNA. Science. 254:437–439.

Ogawa et al., *Sci. Rep.,* 13:42–48, 1973.

Omirulleh et al., *Plant Mol. Biol.,* 21(3):415–428, 1993.

Ow et al., *Science,* 234:856–859, 1986.

Palukaitis et al., *Virology,* 99:145–151, 1979.

Pear, J., Ridge, N., Rasmussen, R., Rose, R. and Houck, C. (1989). Isolation and characterization of a fruit-specific cDNA and the corresponding genomic clone from tomato. Plant Mol. Biol. 13:639–651.

Perlak et al., *Proc. Nat'l Acad. Sci. USA,* 88:3324–3328, 1991.

Perriman et al., *Gene,* 113:157–163, 1992.

Phi-Van et al., *Mol. Cell. Biol.,* 10:2302–2307, 1990.

Piatkowski et al., *Plant Physiol.,* 94:1682–1688, 1990.

Poszkowski et al., *EMBO J.,* 3:2719, 1989.

Potrykus et al., *Mol. Gen. Genet,* 199:183–188, 1985.

Poulsen et al., *Mol. Gen. Genet.,* 205(2):193–200, 1986.

Prasher et al., *Biochem. Biophys. Res. Commun.,* 126(3): 1259–1268, 1985.

Prody et al., *Science,* 231:1577–1580, 1986.

Quigley, Brinkman, Martin, Cerff, *J. Mol. Evol.,* 29(5): 412–421, 1989.

Ralston, English, Dooner, *Genet.,* 119(1):185–197, 1988.

Reece, "The actin gene family of rice (*Oryza sativa* L)," Ph.D. thesis, Cornell University, Ithaca, N.Y., 1988.

Reece, McElroy, Wu, *Plant Mol. Biol.,* 14:621–624, 1990.

Reed et al., *J. Gen. Microbiology,* 130:1–4, 1984.

Reichel et al., *Proc. Nat'l Acad. Sci. USA,* 93 (12) p. 5888–5893. 1996.

Reina et al., *Nucl. Acids Res.,* 18(21):6426, 1990.

Reinhold-Hurek and Shub, *Nature,* 357:173–176, 1992.

Rensburg et al., *J. Plant Physiol.,* 141:188–194, 1993.

Rhodes et al., *Methods Mol. Biol.,* 55:121–131, 1995.

Rick C M (1980) Tomato linkage survey. *Rep Tomato Genet Coop* 30:2–17

Ritala et al., *Plant Mol. Biol.,* 24(2):317–325, 1994.

Robinson, R. and Tomes, M. (1968) Ripening inhibitor: A gene with multiple effects on ripening. Rep. Tomato Genet. Coop. 18:36–37.

Rochester, Winer, Shah, *EMBO J.,* 5:451–458, 1986.

Rogers et al., *Methods Enzymol.,* 153:253–277, 1987.

Rommens, J., Iannuzi, M., Kerem, B., Drumm, M., Melmer, G., Dean, M., Rozmahel, R., Cole, J., Kennedy, D., Hidaka, N., Zsiga, M., Buchwald, M., Riordan, J., Tsui, L. and Collins, F. (1989). Identification of the cystic fibrosis gene: Chromosome walking and jumping. Science. 45:1059–1065.

Sambrook, Fritsch, and Maniatis, *In Molecular Cloning: A Laboratory Manual,* Second edition, Cold Spring Harbor Laboratory, Cold Spring Harbor, N.Y., 1989.

Sauer, *Mol. and Cell. Biol.,* 7: 2087–2096. 1987.

Schwob et al., *Plant J* 4(3):423–432, 1993.

Seymour B. Taylor E, Tucker A (eds) (1993) Biochemistry of Fruit Ripening. Chapman and Hall, London.

Shagan and Bar-Zvi, *Plant Physiol.,* 101:1397–1398, 1993.

Shapiro, *In: Mobile Genetic Elements,* 1983.

Sheehy, R., Kramer, M. and Hiatt, W. (1988) Reduction of polygalacturonase activity in tomato fruit by antisense RNA. PNAS USA. 85:8805–8809.

Sheehy, R., Pearson, J., Brady, C. and Hiatt, W. (1987) Molecular characterization of tomato fruit polygalacturonase. Mol. Gen. Genet. 208:30–36.

Sheen et al., *Plant Journal,* 8(5):777–784, 1995.

Shure et al., *Cell,* 35:225–233, 1983.

Simpson, Filipowicz, *Plant Mol. Bio.,* 32:1–41, 1996.

Simpson, *Science,* 233:34, 1986.

Singsit et al., *Transgenic Res.,* 6(2):169–176, 1997.

Slater, A., Maunders, M., Edwards, K., Schuch, W. and Grierson, D. (1985) Isolation and characterization of cDNA clones for tomato polygalacturonase and other ripeningrelated proteins. Plant Mol. Biol. 5:137–147.

Smith, C., Watson, C., Ray, J., Bird, C., Morris, P., Schuch, W. and Grierson, D. (1988) Antisense RNA inhibition of polygalacturonase gene expression in transgenic tomatoes. Nature. 334:724–726.

Smith, Watson, Bird, Ray, Schuch, Grierson, *Mol. Gen. Genet.,* 224:447–481, 1990.

Souer E, Van Houwelingen A, Kloos D, Mol J, and Koes R. (1996) The no apical meristem gene of petunia is required for pattern formation in embryos and flowers and is expressed at meristem and primordia boundaries. *Cell.* 85: 159–170
Southern, *J. Mol. Biol.*, 98:503–517, 1975.
Spencer et al., *Plant Molecular Biology*, 18:201–210, 1992.
Sprague and Dudley, eds., *Corn and Improvement*, 3rd ed., 1988.
Stalker et al., *Science*, 242:419–422, 1988.
Stief et al., *Nature* 341:343 1989.
Sullivan, Christensen, Quail, *Mol. Gen. Genet.*, 215(3): 431–440, 1989.
Sutcliffe, *Proc. Nat'l Acad. Sci. USA*, 75:3737–3741, 1978.
Symons, *Annu. Rev. Biochem.*, 61:641–671, 1992.
Tanksley et al., *Bio/Technology*, 7:257–264, 1989.
Tarczynski et al., *Proc. Nat'l Acad. Sci. USA*, 89:1–5, 1992.
Tarczynski et al., *Science*, 259:508–510, 1993.
Thillet et al., *J. Biol. Chem.*, 263:12500–12508, 1988.
Thompson et al., *The EMBO Journal*, 6(9):2519–2523, 1987.
Thompson, Drayton, Frame, Wang, Dunwell, *Euphytica*, 85(1–3):75–80, 1995.
Tian, Sequin, Charest, *Plant Cell Rep.*, 16:267–271, 1997.
Tigchelaar, E., McGlasson, W. and Buescher, R. (1978) Genetic regulation of tomato fruit ripening. HortSci. 13:508–513.
Tigchelaar, E., Tomes, M., Kerr, E. and Barman, R. (1973) A new fruit ripening mutant, non-ripening (no0. Rep. Tomato Genet. Coop. 23:33.
Tingay et al., *The Plant Journal* v. 11 (6) p. 1369–1376. 1997.
Tomes et al., *Plant. Mol. Biol.* 14(2):261–268, 1990.
Tomic et al., *Nucl. Acids Res.*, 12:1656, 1990.
Torbet, Rines, Somers, *Crop Science*, 38(1):226–231, 1998.
Torbet, Rines, Somers, *Plant Cell Reports*, 14(10):635–640, 1995.
Toriyama et al., *Theor Appl. Genet.*, 73:16, 1986.
Tsukada; Kusano; Kitagawa, *Plant Cell Physiol.*, 30(4) 599–604, 1989.
Tucker, M. and Laties, G. (1984) Interrelationship of gene expression, polysome prevalence, and respiration during ripening of ethylene and/or cyanide-treated avocado fruit. Plant Physiol. 74:307–315.
Twell et al., Plant Physiol 91:1270–1274, 1989.
Uchimiya et al., *Mol. Gen. Genet.*, 204:204, 1986.
Ugaki et al., *Nucl. Acid Res.*, 19:371–377, 1991.
Upender, Raj, Weir, *Biotechniques* 18(1):29–30, 1995.

Van der Krol, Mur, Beld, Mol, Stuitje, *Plant Cell*, 2:291–99, 1990.
Van Eck; Blowers; Earle, *Plant Cell Reports*, 14(5): 299–304, 1995.
Van Tunen et al., *EMBO J.*, 7:1257, 1988.
Vasil et al., *Plant Physiol.*, 91:1575–1579, 1989.
Vernon and Bohnert, *The EMBO J.*, 11:2077–2085, 1992.
Vodkin et al., *Cell*, 34:1023, 1983.
Vogel, Dawe, Freeling, *J. Cell. Biochem.*, (Suppl. 0) 13:Part D, 1989.
Walker et al., *Proc. Nat'l Acad. Sci. USA*, 84:6624–6628, 1987.
Wandelt and Feix, *Nucl. Acids Res.*, 17(6):2354, 1989.
Wang et al., *Molecular and Cellular Biology*, 12(8): 3399–3406, 1992.
Watrud et al., *In: Engineered Organisms and the Environment*, 1985.
Watson and Ramstad, eds., *Corn: Chemistry and Technology*, 1987.
Wenzler et al., *Plant Mol. Biol.*, 12:41–50, 1989.
Williams, J., Kubelik, A., Livak, K., Rafalski, J. and Tingey, S. (1990) DNA polymorphisms amplified by arbitrary primers are useful as genetic markers. Nucleic Acids Res. 1 8:6531–6535.
Withers and King, *Plant Physiol.*, 64:675–678, 1979.
Wolter et al., *The EMBO J.*, 4685–4692, 1992.
Xiang and Guerra, *Plant Physiol.*, 102:287–293, 1993.
Xu et al., *Plant Physiol.*, 110:249–257, 1996.
Yamada et al., *Plant Cell Rep.*, 4:85, 1986.
Yamaguchi-Shinozaki et al., *Plant Cell Physiol.*, 33:217–224, 1992.
Yang and Russell, *Proc. Nat'l Acad. Sci. USA*, 87:4144–4148, 1990.
Yen, H., Shelton, A., Howard, L. Vrebalov, J. and Giovannoni, J. (1997) The tomato high pigment (hp) locus maps to chromosome 2 and influences plastome copy number and fruit quality. Theoretical and Applied Genetics 95: 1069–1079
Yuan and Altman, *Science*, 263: 1269–1273, 1994.
Yuan et al., *Proc. Nat'l Acad. Sci. USA*, 89:8006–8010, 1992.
Zhang, McElroy, Wu, *The Plant Cell*, 3: 1155–1165, 1991.
Zheng and Edwards, *J. Gen. Virol.*, 71:1865–1868, 1990.
Zhou; Stiff; Konzak, *Plant Cell Reports*, 12(11).612–616, 1993.
Zukowsky et al., *Proc. Nat'l Acad Sci. USA*, 80:1101–1105, 1983.

---

What is claimed is:

1. An expression vector comprising a NOR gene operably linked to a heterologous promoter, wherein said NOR gene is oriented antisense relative to said heterologous promoter, and wherein said NOR gene encodes the polypeptide sequence encoded by SEQ ID NO:6.

2. A method of altering the fruit ripening of a tomato plant comprising the steps of:
   (i) obtaining an expression vector comprising a NOR gene in antisense orientation, wherein said NOR gene encodes the polypeptide sequence encoded by SEQ ID NO:6;
   (ii) transforming a recipient tomato plant cell with said expression vector; and
   (iii) regenerating a transgenic tomato plant from said recipient plant cell, wherein the fruit ripening of said tomato plant is altered based on the expression of said NOR gene in antisense orientation.

3. The method of claim 2, wherein said step of transforming comprises a method selected from the group consisting of microprojectile bombardment, PEG mediated transformation of protoplasts, electroporation, silicon carbide fiber mediated transformation, or Agrobacterium-mediated transformation.

4. The method of claim 3, wherein said step of transforming comprises Agrobacterium-mediated transformation.

5. The expression vector of claim 1, wherein said NOR gene comprises from about 17 to about 1209 contiguous nucleotides of the nucleic acid sequence of SEQ ID NO:6.

6. The expression vector of claim 1, wherein said NOR gene comprises from about 25 to about 1209 contiguous nucleotides of the nucleic acid sequence of SEQ ID NO:6.

7. The expression vector of claim 1, wherein said NOR gene comprises from about 30 to about 1209 contiguous nucleotides of the nucleic acid sequence of SEQ ID NO:6.

8. The expression vector of claim 1, wherein said NOR gene comprises from about 40 to about 1209 contiguous nucleotides of the nucleic acid sequence of SEQ ID NO:6.

9. The expression vector of claim 1, wherein said NOR gene comprises from about 60 to about 1209 contiguous nucleotides of the nucleic acid sequence of SEQ ID NO:6.

10. The expression vector of claim 1, wherein said NOR gene comprises from about 100 to about 1209 contiguous nucleotides of the nucleic acid sequence of SEQ ID NO:6.

11. The expression vector of claim 1, wherein said NOR gene comprises from about 200 to about 1209 contiguous nucleotides of the nucleic acid sequence of SEQ ID NO:6.

12. The expression vector of claim 1, wherein said NOR gene comprises from about 400 to about 1209 contiguous nucleotides of the nucleic acid sequence of SEQ ID NO:6.

13. The expression vector of claim 1, wherein said NOR gene comprises from about 600 to about 1209 contiguous nucleotides of the nucleic acid sequence of SEQ ID NO:6.

14. The expression vector of claim 1, wherein said NOR gene comprises from about 800 to about 1209 contiguous nucleotides of the nucleic acid sequence of SEQ ID NO:6.

15. The expression vector of claim 1, wherein said NOR gene comprises from about 1000 to about 1209 contiguous nucleotides of the nucleic acid sequence of SEQ ID NO:6.

16. The expression vector of claim 1, wherein said NOR gene comprises the nucleic acid sequence of SEQ ID NO:6.

17. The method of claim 2, wherein said NOR gene comprises from about 17 to about 1209 contiguous nucleotides of the nucleic acid sequence of SEQ ID NO:6.

18. The method of claim 2, wherein said NOR gene comprises from about 25 to about 1209 contiguous nucleotides of the nucleic acid sequence of SEQ ID NO:6.

19. The method of claim 2, wherein said NOR gene comprises from about 30 to about 1209 contiguous nucleotides of the nucleic acid sequence of SEQ ID NO:6.

20. The method of claim 2, wherein said NOR gene comprises from about 40 to about 1209 contiguous nucleotides of the nucleic acid sequence of SEQ ID NO:6.

21. The method of claim 2, wherein said NOR gene comprises from about 60 to about 1209 contiguous nucleotides of the nucleic acid sequence of SEQ ID NO:6.

22. The method of claim 2, wherein said NOR gene comprises from about 100 to about 1209 contiguous nucleotides of the nucleic acid sequence of SEQ ID NO:6.

23. The method of claim 2, wherein said NOR gene comprises from about 200 to about 1209 contiguous nucleotides of the nucleic acid sequence of SEQ ID NO:6.

24. The method of claim 2, wherein said NOR gene comprises from about 400 to about 1209 contiguous nucleotides of the nucleic acid sequence of SEQ ID NO:6.

25. The method of claim 2, wherein said NOR gene comprises from about 600 to about 1209 contiguous nucleotides of the nucleic acid sequence of SEQ ID NO:6.

26. The method of claim 2, wherein said NOR gene comprises from about 800 to about 1209 contiguous nucleotides of the nucleic acid sequence of SEQ ID NO:6.

27. The method of claim 2, wherein said NOR gene comprises from about 1000 to about 1209 contiguous nucleotides of the nucleic acid sequence of SEQ ID NO:6.

28. The method of claim 2, wherein said NOR gene comprises the nucleic acid sequence of SEQ ID NO:6.

\* \* \* \* \*

SEQUENCE LISTING

<160> NUMBER OF SEQ ID NOS: 7

<210> SEQ ID NO 1
<211> LENGTH: 1211
<212> TYPE: DNA
<213> ORGANISM: Tomato

<400> SEQUENCE: 1

```
aggtcaactc aaacatcgta aattgtgatt tctttatgga aagtacggat tcatcaaccg      60
ggacacgtca tcagcctcaa ctcccaccgg ggtttcgatt ccacccgacg gacgaagaac     120
tcatcgtcca ctacctcaaa aaaccagtcg ccggcgctcc gattccggtg gatattattg     180
```

-continued

```
gtgaaattga tctttataag tttgatccat gggaactccc tgctaaggca atattcggag      240
agcaagaatg gttctttttt agtccaagag atagaaaata tcctaacggg gcgaggccaa      300
atcgggctgc aacatcggt tattggaagg ctaccggaac cgacaagccg gtttttactt      360
ccggtggaac acaaaggtt ggggtaaaaa aggcgctcgt ttttacggc ggtaaaccac      420 caaaagggt aaaaactaat tggatcatgc atgaatacag agttgtagaa aataaaacaa      480
ataacaagcc acttggttgt gataatattg ttgccaacaa aaaggatct ttgaggctag      540 atgattgggt tttatgtcga atttacaaga agaataacac acaaaggtcc atagatgatt      600
tgcatgatat gttgggatcg ataccacaaa atgtaccaaa ttcatatta caaggaataa      660 agccttcaaa ctatggtaca atattgctcg aaaatgaatc gaatatgtac gatggaatta      720
tgaataacac gaacgatatt atcaacaata ataatagatc cattccacaa atatcgtcaa      780
agagaacgat gcatggaggt ttgtattgga ataacgacga agcaacaaca acaacaacaa      840
ctattgatag gaaccattct ccaaatacaa aaggttttcc ttgttgagaa caacgaggac      900
gatggactta acatgaataa tatttcgcga attacaaatc atgaacaaag tagctccatt      960
gccaatttcc tgagccagtt tcctcaaaat ccttggattc aacaacaaca acaacaacaa     1020
gaagaagtat tgggatctct taatgatggg gtcgtctttc gacaaccta taatcaagtt     1080 actggcatga attggtactc ttaaagatat aaaaggcaa aaaatagtta gccctgtaaa     1140
atcaatcgat caatcaatca tagatatatt atatatggat ttcgttaaaa aaaaaaaaa     1200 aaaaaaaaa a                                                          1211

<210> SEQ ID NO 2
<211> LENGTH: 1097
<212> TYPE: DNA
<213> ORGANISM: Tomato

<400> SEQUENCE: 2
aaaaggagct aagtttaata atttttttt ataaaaaaa aaaaactttt tttgaagatg       60
ggaagaggaa aagttgaatt aagaaaaata gagaataaaa taaatagaca agtaacattt      120
tcaaagagaa gaggtggatt agtgaaaaaa gctcatgaaa tttcagtttt atgtgatgct      180
gaagttgctt taattgtttt ctctcaaaag ggaaaaatct ttgagtattc ttctgattca      240
tgtatggaac aaattcttga acgatatgaa agatactcat atgcagagag acgtttgctt      300
gcaaataatt ctgaatcacc ggtgcaggaa aactggagct tggaatatac taaactcaag      360
gctaggattg atctccttca aaggaaccac aagcattata tgggggaaga tcttgattca      420
atgagcttga aggacttgca aaacttggaa caacagcttg attctgctct taagctaaat      480
tcgatcgaga agaaccact catgcatgaa tcaatctctg aactgcagaa aaaggaaaga      540
gctatcctag aggagaataa catgctaacc aagaagatta aggagaagga taagatagta      600
gaacagcaag gtgaatggca ccagcaaact aatcaagttt ctacttcaac atctttcctc      660
ttacaaccac atcaatgcct aaatatggga ggtaattacc aagatgaagt agcagaagca      720
aggaggaata atgagcttga cctaaatctt gattcattat atccacttta caacatgaat      780
aaacatctat gaataatttc actctttgct aatcgcttga aacgttgaaa ggagctcact      840
atcaggacag acaaatgagt ataagcgatt agcgataaaa actctatgcg agaggaaatt      900
atatatgatg ttaattaatc tatgcttgag aaattcttaa ttatatatat tgagtgtctt      960
tatattgata tgcatgtata gaaccttatt attatgaatt tctatgtatt aatgtttaag     1020
tatgttaaaa cttaattgtt aatggaatca agtccattct ctttgtatcc aaaaaaaaaa     1080
```

```
aaaaaaaaaa aaaaaaa                                                    1097

<210> SEQ ID NO 3
<211> LENGTH: 1138
<212> TYPE: DNA
<213> ORGANISM: Tomato

<400> SEQUENCE: 3
ttttcttctt gactagggaa ccattagatt ttaaagacat taaatctatt accttaccc       60 taagaaataa gaagatgtaa agtagaagag aaaacaacca aaaccatata tatacatata     120
tataattaca ttatattgtc ttataacatg tagtctttta aggaaaaaca aatttagaaa     180
aaaaataata ttattttaca tttttttttc ttcatacaat atgggtagag ggaaagtaga     240
attgaagaga attgagaaca aaataaatag acaagttacc tttgcaaaga gaagaaatgg     300
actcctaaag aaagcttatg aactttctat actttgtgat gctgaaattg ctcttattat     360
ttcctctagt cgtggcaagc tttatgaatt ttgcagcaat tcaagtatgt ccaagacatt     420
ggagagatac cacagataca attatggtac acttgaagga acccaaactt catcagattc     480
acagaacaac taccaggagt atttgaagct taaaacaaga gtggaaatgt tacaacagtc     540
tcaaaggcat ttgctaggtg aggatttggg acaattgggc acaaaagact tggaacagct     600
tgaacgtcaa ttggattcat cattgaggca aattaggtca acaaagacac aacacattct     660
tgatcaactt gctgaacttc aacaaaagga caatctctt actgaaatga caaatctt      720 gagaataaag ttggaagaac ttggtgttac ctttcaaaca tcatggcatt gtggtgagca     780
aagtgtacaa tatagacatg aacagccttc tcatcatgag ggattttttc aacatgtaaa     840
ttgcaataat acattgccta taagcaccat caacacatgg atgctactgg agttgtacct     900
ggatggatgc tttgaatttg gagtatatgg agagaaaaaa tcctcttagt atacaagtta     960
tttattttta ttaaaaaaat aagttagatg gagaattata tatatcatac tttaaagaac    1020
ttatattgtt tgaatgtttt agctagcaaa cactttggat tatatataat attgtgatat    1080
atttattgtc aagaagatat ggcaatattg ataacactat attttgaaa aaaaaaa      1138

<210> SEQ ID NO 4
<211> LENGTH: 1119
<212> TYPE: DNA
<213> ORGANISM: Tomato

<400> SEQUENCE: 4
gggaaccatt agattttaaa gacattaaat ctattaccct taccctaaga ataagaagat      60
gtaaagtata agagaaaaca accaaaacca tatatataca tatatataat tacattatat     120
tgtcttataa catatagtct tttaaggaaa acaaattta gaaaaaaaat aatattattt     180
tacatttttt ttcttcata caatatgggt agagggaaag tagaattgaa gagaattgag     240
aacaaaataa atagacaagt taccttgca agagaagaa atggactcct aaagaaagct     300
tatgaacttt ctatactttg tgatgctgaa attgctctta ttattttctc tagtcgtggc     360
aagctttatg aattttgcag caattcaagt atgtccaaga cattggagag ataccacaga     420
tacaattatg gtacacttga aggaacccaa acttcatcag attcacagaa caactaccaa     480
gagtatttga agcttaaaac aagagtggaa atgttacaac agtctcaaag gcatttgcta     540
ggtgaggatt tgggacaatt gggcacaaaa gacttggaac agcttgaacg tcaattggat     600
tcatcattga ggcaattagg tacacaagac acacccattc ttgatcaact tgctgaactt     660
```

-continued

| | |
|---|---|
| caccaaaagg aacaatctct tactgaaatg aacaaatctt tgagaataaa gttggaagaa | 720 |
| cttggtgtta cctttccaac atcatggcat tgtggtgagc aaagtgtaca atatagacat | 780 |
| gaacagcctt tccatcatga gggattttc aacatgtaca ttgcaataat acattgccta | 840 |
| tacgcaccat caacacatga tgctactgga gttgtacctg gatggatgct ttgaatttgg | 900 |
| agtatatgga gagaaaaaat cctcttagtt atacaagtta tttattttta ttaaaaaaat | 960 |
| aagttagatg gagaattata tatatcatac tttaagaac ttatattgtt tgaatgtttt | 1020 |
| agctagcaaa cactttggat tatatataat attgtgatat atttattgtc aagaagagta | 1080 |
| tggcaatatt gataacacta tatttttgaa aaaaaaaaa | 1119 |

<210> SEQ ID NO 5
<211> LENGTH: 1191
<212> TYPE: DNA
<213> ORGANISM: Tomato

<400> SEQUENCE: 5

| | |
|---|---|
| gtcgacggga accattagat tttaaagaca ttaaatctat taccttacc ctaagaataa | 60 |
| gaagatgtaa agtagaagag aaacaacca aaccatata tatacatata taaattaca | 120 |
| ttatattgtc ttataacata tagtcttta aggaaaaaca aatttagaaa aaaataata | 180 |
| ttattttaca ttttttttc ttcatacaat atgggtagag ggaaagtaga attgaagaga | 240 |
| attgagaaca aataaatag acaagttacc tttgcaaaga gaagaaatgg actcctaaag | 300 |
| aaagcttatg aactttctat actttgtgat gctgaaattg ctcttattat tttctctagt | 360 |
| cgtggcaagc tttatgaatt tgcagcaat tcaagtatgt ccaagacatt ggagagatac | 420 |
| cacagataca attatggtac acttgaagga acccaaactt catcagattc acagaacaac | 480 |
| taccaagagt atttgaagct taaaacaaga gtggaaatgt tacaacagtc tcaaaggcat | 540 |
| ttgctaggtg aggatttggg acaattgggc acaaaagact tggaacagct tgaacgtcaa | 600 |
| ttggattcat cattgaggca aattaggtca acaaagacac aacacattct tgatcaactt | 660 |
| gctgaacttc aacaaaagga acaatctctt actgaaatga caaatcttt gagaataaag | 720 |
| ttggaagaac ttggtgttac ctttcaaaca tcatggcatt gtggtgagca aagtgtacaa | 780 |
| tatagacatg aacagcctt tcatcatgag ggatttttc aacatgtaaa ttgcaataat | 840 |
| acattgccta taagttacgg atacgataat gtacaacccg aaaatgcagc accatcaaca | 900 |
| catgatgcta ctggagttgt acctggatgg atgctttgaa tttggagtat atggagagaa | 960 |
| gaaatcctct tagttataca agttatttat ttttattaaa aaataagtt agatggaaa | 1020 |
| ttatatatat catactttaa agaacttata tgtttgaat gttttagcta gcaaacactt | 1080 |
| tggattatat ataatattgt gatatattta ttgtcaagaa gagtatggca atattgataa | 1140 |
| cactaaaaaa aaaaaaaaa aaaaaaaaa aaaaaaaag gaaaaaaaa a | 1191 |

<210> SEQ ID NO 6
<211> LENGTH: 1209
<212> TYPE: DNA
<213> ORGANISM: Tomato

<400> SEQUENCE: 6

| | |
|---|---|
| aggtcaactc aaacatcgta aattgtgatt tcttatgga agtacggat tcatcaacca | 60 |
| ggacacgtca tcagcctcaa ctcccaccgg ggtttcgatt ccaccgacg acgaagaac | 120 |
| tcatcgtcca ctacctcaaa aaacgagtcg ccggcgctcc gattccggtg atattattg | 180 |
| gtgaaattga tctttataag tttgatccat gggaactccc tggtaaggca atattcggag | 240 |

```
agcaagaatg gttctttttt agtccaagag atagaaaata tcctaacggg gcgaggccaa      300
atcgggctgc aacatcgggt tattggaagg ctaccggaac cgacaagccg ttttttactt      360
ccggtggaac acaaaaggtt gggtaaaaa aggcgctcgt tttttacggc ggtaaaccac       420 caaaagggt aaaaactaat tggatcatgc atgaatacag agttgtagaa aataaaacaa       480
ataacaagcc acttggttgt gataatattg ttgccaacaa aaaaggatct ttgaggctag      540
atgattgggt tttatgtcga atttacaaga agaataacac acaaaggtcc atagatgatt     600
tgcatgatat gttgggatcg ataccacaaa atgtaccaaa ttcaatatta caaggaataa    660
agccttcaaa ctatggtaca atattgctcg aaaatgaatc gaatatgtac gatggaatta     720
tgaataacac gaacgatatt atcaacaata ataatagatc cattccacaa atatcgtcaa    780
agagaacgat gcatggaggt ttgtattgga ataacgacga agcaacaaca acaacaacaa   840
ctattgatag gaaccattct ccaaatacaa aaggttcct tgttgagaac aacgaggacg      900
atggacttaa catgaataat atttcgcgaa ttacaaatca tgaacaaagt agctccattg    960
ccaatttcct gagccagttt cctcaaaatc cttcgattca acaacaacaa caacaacaag   1020
aagaagtatt gggatctctt aatgatgggg tcgtctttcg acaaccttat aatcaagtta   1080
ctggcatgaa ttggaatcac aaagatataa aaggcaaaaa aatagttagc cctgtaaaat    1140
caatcgatca atcaatcata gatatattat atatggattt cgttaaaaaa aaaaaaaaaa     1200
aaaaaaaaa                                                              1209

<210> SEQ ID NO 7
<211> LENGTH: 2680
<212> TYPE: DNA
<213> ORGANISM: Tomato

<400> SEQUENCE: 7
aggtcaactc aaacatcgta aattgtgatt tctttatgga aagtacggat tcatcaacca      60
ggacacgtca tcagcctcaa ctcccaccgg ggtttcgatt ccaccgacg gacgaagaac      120 tcatcgtcca ctacctcaaa aaacgagtcg ccggcgctcc gattccggtg gatattattg     180
gtgaaattga tctttataag tttgatcctg ggaactccct ggtactattt tcaccactat     240
actatatttt cttgccctat aacttatata taggggaaaa agatcggagt cagcgatgaa    300
caattattgt gtctaaatta aattttaaat atgcaataga ttggtgacga atttcgttgc    360
taattaattt tttagtgata aattaatatt tttccccttt ttaatcttca tgttttttat    420
cacaaagttt tctatgacca acttataaag atttgaactc gatcaatttt ttttttagaa    480
tgaatgaact tatgttatat atagtgtatat tttaaatgct ttttttatatt ttcaaaagat  540 atccacgata acgtgtaaaa agtgaatttg caaaaaaaaa atgtagtacc ttttattaa    600 ttttattgta gataatttag attttaattt tgaatttgtt taatttaaat tctgaatcgt    660
ataatattta tttaattct attttttgag ttttttttg gagggtgctt aaaaagtagt     720
attcacaaat ataagtagt ggacaaacat aaagtagtgg acccataatt tattttttta    780
aaaattatat taaaactatt tgttaagttt aaattctgaa ttatcttctt atcatgtgtt    840
taacgcagct aaggcaatat tcggagagca agaatggttc ttttttagtc caagagatag   900
aaaatatcct aacggggcga ggccaaatcg ggctgcaaca tcgggttatt ggaaggctac    960
cggaaccgac aagccggttt ttacttccgg tggaacacaa aaggttgggg taaaaaaggc   1020
gctcgttttt tacggcggta aaccaccaaa agggtaaaa actaattgga tcgtgcatga   1080
```

-continued

```
atacagagtt gtagaaaata aaacaaataa caagccactt ggttgtgata atattgttgc   1140
caacaaaaaa ggatctttga gggtaagtcc taaattttgc atcgaaacta atttctctat   1200
cgtatcagat agggataaga tatacgtata ctctaatctc cttgaaccac acaagtacta   1260
tactagatat gttgttgttg tagatgactt gattcaactt tcaaattttt gatgaaaatg   1320
tttaagttat atataccata tatatatagg cgtagctaaa aatttcgata aggggttta    1380 aatctgaaaa aatggatata cgaaatagcc gaaagaggtt cgacatagat tattttaacc   1440
atataaaaat aatacaattt tcatatatat atacgccgtg gttaatatga ggaatatttt   1500
atactattaa tgtactttaa ccaggggcgg ctctagagtt gatgaaccct ctcagcgaaa   1560
atttacgttg tatatttaag gtaccttta ataattttg tatttatata ttaattttga    1620
acctcttgaa tataagatta gacgttgact tagtggttc aggggttcaa atcactattc    1680 ttttttcct aaccccctta atgaaaatcc tgaatcggcc actaacttta actggttata    1740
gaaggttaat cttactagaa aaaagcatga aattctaacc gacaaagatg tagtcgccca   1800
gttagataag acgtttaaat tgggcggata gagttacttt attttcact gtcatatgtt    1860 actatatatt gacacttcac ttaaagagtt atcatatcga tattttact attagtgtac    1920 ataacacaaa ctcgaataaa ttcaatgttt cattagctag ttaattagtc taactttttt   1980
aaaaaaaaat attttctta ctccacacta ttttatttta tttttttgca gctagatgat    2040
tgggttttat gtcgaattta caagaagaat aacacacaaa ggtccataga tgatttgcat   2100
gatatgttgg gatcgatacc acaaaatgta ccaaattcaa tattacaagg aataaagcct   2160
tcaaactatg gtacaatatt gctcgaaaat gaatcgaata tgtacgatgg aattatgaat   2220
aacacgaacg atattatcaa caataataat agatccattc cacaaatatc gtcaaagaga   2280
acgatgcatg gaggtttgta ttggaataac gacgaagcaa caacaacaac aacaactatt   2340
gataggaacc attctccaaa tacaaaaagg ttccttgttg agaacaacga ggacgatgga   2400
cttaacatga ataatatttc gcgaattaca aatcatgaac aaagtagctc cattgccaat   2460
ttcctgagcc agtttcctca aaatccttcg attcaacaac aacaacaaca acaagaagaa   2520
gtattgggat ctcttaatga tggggtcgtc tttcgacaac cttataatca agttactggc   2580
atgaattgga atcactaaag atataaaaag gcaaaaaata gttagccctg taaaatcaat   2640
cgatcaatca atcatagata tattatatat ggatttcgtt                         2680
```